United States Patent
Mitsuzumi et al.

(10) Patent No.: US 6,346,394 B1
(45) Date of Patent: *Feb. 12, 2002

(54) RECOMBINANT THERMOSTABLE ENZYME WHICH RELEASES TREHALOSE FROM NON-REDUCING SACCHARIDE

(75) Inventors: Hitoshi Mitsuzumi; Michio Kubota; Toshiyuki Sugimoto, all of Okayama (JP)

(73) Assignee: Kabushiki Kaisha Hayashibara Seibutsu Kagaku Kenkyujo, Okayama (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/055,210

(22) Filed: Apr. 6, 1998

Related U.S. Application Data

(60) Continuation of application No. 08/798,269, filed on Feb. 11, 1997, which is a division of application No. 08/505,377, filed on Jul. 21, 1995, now Pat. No. 5,856,146.

(30) Foreign Application Priority Data

| Jul. 21, 1994 | (JP) | ................................. 6-190180 |
| Apr. 11, 1995 | (JP) | ................................. 7-109128 |
| Jul. 4, 1995 | (JP) | ................................. 7-189760 |

(51) Int. Cl.⁷ .......................... C12N 9/24; C12P 19/18; C07K 14/195
(52) U.S. Cl. .................... 435/69.1; 435/69.2; 435/71.1; 435/71.2; 435/183; 435/200; 435/252.33; 435/97; 435/320.1; 536/23.1; 536/23.2; 536/23.7
(58) Field of Search .............................. 435/69.2, 69.1, 435/71.1, 71.2, 183, 97, 200, 252.33, 320.1; 536/23.2, 23.1, 23.7

(56) References Cited

U.S. PATENT DOCUMENTS

| 4,521,252 A | 6/1985 | Miyake et al. ................. 127/46 |
| 5,591,612 A | 1/1997 | Maruta et al. .............. 435/100 |

FOREIGN PATENT DOCUMENTS

| EP | 0 606 753 A2 | 12/1983 |
| GB | 2106912 | 8/1982 |
| JP | 50-1544858 | 12/1975 |
| JP | 58-23799 | 2/1983 |
| JP | 58-72598 | 4/1983 |
| JP | 58-216695 | 12/1983 |

OTHER PUBLICATIONS

Laemmli, U.K., "Cleavage of Structural Proteins during the Assembly of the Head of Bateriophage T4"; Nature; vol. 227; pp. 680–685; Aug. 15, 1970.

Licia et al, Thermostable Amylolytic Activity from Sulfolbus solfataricus; Biotech Forum Europe; vol. 8, No. 4, pp. 201–203; 1991.

Reeck et al, "Homology" in Proteins and Nucleic Acids: A Terminology Muddle and a Way out of it, *Cell,* 50:667 (1987).

Sambrook et al, *Molecular Cloning: A Laboratory Manual;* Cold Spring Harbour Laboratory Press; pp. v–xxxii; 1989.

The Amylase Research Society of Japan, editors; *Handbook of Amylases and Related Enzymes: Their Sources, Isolation Methods, Properties and Applications;* Permagon Press; pp. xi–71; 1988.

*Primary Examiner*—Donna C. Wortman
*Assistant Examiner*—Mary K. Zeman
(74) *Attorney, Agent, or Firm*—Browdy and Neimark

(57) ABSTRACT

Disclosed is a recombinant thermostable enzyme which has a molecular weight of about 54,000–64,000 daltons and a pI of about 5.6–6.6, and releases trehalose from non-reducing saccharides having a trehalose structure as an end unit and a degree of glucose polymerization of at least 3. The enzyme has a satisfactorily-high thermostability, i.e. it is not substantially inactivated even when incubated in an aqueous solution (pH 7.0) at 85° C. for 60 min, and this facilitates the production of trehalose on an industrial scale and in a satisfactorily-high yield.

17 Claims, 5 Drawing Sheets

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 556 amino acids
      (B) TYPE: amino acid
      (D) TOPOLOGY: linear (ii) MOLECULE TYPE: protein (xi) SEQUENCE DESCRIPTION: SEQ ID NO:1:

```
Met Phe Ser Phe Gly Gly Asn Ile Glu Lys Asn Lys Gly Ile Phe Lys
 1               5                  10                  15

Leu Trp Ala Pro Tyr Val Asn Ser Val Lys Leu Lys Leu Ser Lys Lys
             20                  25                  30

Leu Ile Pro Met Glu Lys Asn Asp Glu Gly Phe Phe Glu Val Glu Ile
         35                  40                  45

Asp Asp Ile Glu Glu Asn Leu Thr Tyr Ser Tyr Ile Ile Glu Asp Lys
     50                  55                  60

Arg Glu Ile Pro Asp Pro Ala Ser Arg Tyr Gln Pro Leu Gly Val His
 65                  70                  75                  80

Asp Lys Ser Gln Leu Ile Arg Thr Asp Tyr Gln Ile Leu Asp Leu Gly
             85                  90                  95

Lys Val Lys Ile Glu Asp Leu Ile Ile Tyr Glu Leu His Val Gly Thr
            100                 105                 110

Phe Ser Gln Glu Gly Asn Phe Lys Gly Val Ile Glu Lys Leu Asp Tyr
        115                 120                 125

Leu Lys Asp Leu Gly Ile Thr Gly Ile Glu Leu Met Pro Val Ala Gln
    130                 135                 140

Phe Pro Gly Asn Arg Asp Trp Gly Tyr Asp Gly Val Phe Leu Tyr Ala
145                 150                 155                 160

Val Gln Asn Thr Tyr Gly Gly Pro Trp Glu Leu Ala Lys Leu Val Asn
                165                 170                 175

Glu Ala His Lys Arg Gly Ile Ala Val Ile Leu Asp Val Val Tyr Asn
            180                 185                 190

His Ile Gly Pro Glu Gly Asn Tyr Leu Leu Gly Leu Gly Pro Tyr Phe
        195                 200                 205

Ser Asp Arg Tyr Lys Thr Pro Trp Gly Leu Thr Phe Asn Phe Asp Asp
    210                 215                 220

Arg Gly Cys Asp Gln Val Arg Lys Phe Ile Leu Glu Asn Val Glu Tyr
225                 230                 235                 240

Trp Phe Lys Thr Phe Lys Ile Asp Gly Leu Arg Leu Asp Ala Val His
                245                 250                 255

Ala Ile Phe Asp Asn Ser Pro Lys His Ile Leu Gln Glu Ile Ala Glu
            260                 265                 270

Lys Ala His Gln Leu Gly Lys Phe Val Ile Ala Glu Ser Asp Leu Asn
        275                 280                 285

Asp Pro Lys Ile Val Lys Asp Asp Cys Gly Tyr Lys Ile Asp Ala Gln
    290                 295                 300

Trp Val Asp Asp Phe His His Ala Val His Ala Phe Ile Thr Lys Glu
305                 310                 315                 320

Lys Asp Tyr Tyr Tyr Gln Asp Phe Gly Arg Ile Glu Asp Ile Glu Lys
                325                 330                 335

Thr Phe Lys Asp Val Phe Val Tyr Asp Gly Lys Tyr Ser Arg Tyr Arg
            340                 345                 350

Gly Arg Thr His Gly Ala Pro Val Gly Asp Leu Pro Pro Arg Lys Phe
        355                 360                 365

Val Val Phe Ile Gln Asn His Asp Gln Val Gly Asn Arg Gly Asn Gly
    370                 375                 380

Glu Arg Leu Ser Ile Leu Thr Asp Lys Thr Thr Tyr Leu Met Ala Ala
385                 390                 395                 400
```

```
Thr Leu Tyr Ile Leu Ser Pro Tyr Ile Pro Leu Ile Phe Met Gly Glu
            405                 410                 415

Glu Tyr Tyr Glu Thr Asn Pro Phe Phe Phe Ser Asp Phe Ser Asp
            420                 425                 430

Pro Val Leu Ile Lys Gly Val Arg Gly Arg Leu Lys Glu Asn Asn
            435                 440                 445

Gln Met Ile Asp Pro Gln Ser Glu Glu Ala Phe Leu Lys Ser Lys Leu
    450                 455                 460

Ser Trp Lys Ile Asp Glu Glu Val Leu Asp Tyr Tyr Lys Gln Leu Ile
465                 470                 475                 480

Asn Ile Arg Lys Arg Tyr Asn Asn Cys Lys Arg Val Lys Glu Val Arg
                485                 490                 495

Arg Glu Gly Asn Cys Ile Thr Leu Ile Met Glu Lys Ile Gly Ile Ile
            500                 505                 510

Ala Ser Phe Asp Asp Ile Val Ile Asn Ser Lys Ile Thr Gly Asn Leu
            515                 520                 525

Leu Ile Gly Ile Gly Phe Pro Lys Lys Leu Lys Asp Glu Leu Ile
            530                 535                 540

Lys Val Asn Arg Gly Val Gly Val Tyr Gln Leu Glu
545                 550                 555

(2) INFORMATION FOR SEQ ID NO:2:

(i) SEQUENCE CHARACTERISTICS:
        (A) LENGTH: 1668 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

ATGTTTTCGT TCGGTGGAAA TATTGAAAAA AATAAAGGTA TCTTTAAGTT ATGGGCACCT       60

TATGTTAATA GTGTTAAGCT GAAGTTAAGC AAAAAACTTA TTCCAATGGA AAAAAACGAT      120

GAGGGATTTT TCGAAGTAGA AATAGACGAT ATCGAGGAAA ATTTAACCTA TTCTTATATT      180

ATAGAAGATA AGAGAGAGAT ACCTGATCCC GCATCACGAT ATCAACCTTT AGGAGTTCAT      240

GACAAATCAC AACTTATAAG AACAGATTAT CAGATTCTTG ACCTTGGAAA AGTAAAAATA      300

GAAGATCTAA TAATATATGA ACTCCACGTT GGTACTTTTT CCCAAGAAGG AAATTTCAAA      360

GGAGTAATAG AAAAGTTAGA TTACCTCAAG GATCTAGGAA TCACAGGAAT TGAACTGATG      420

CCTGTGGCAC AATTTCCAGG GAATAGAGAT TGGGGATACG ATGGTGTTTT TCTATACGCA      480

GTTCAAAATA CTTATGGCGG ACCATGGGAA TTGGCTAAGC TAGTAAACGA GGCACATAAA      540

AGGGGAATAG CCGTAATTTT GGATGTTGTA TATAATCATA TAGGTCCTGA GGGAAATTAC      600

CTTTTAGGAT TAGGTCCTTA TTTTTCAGAC AGATATAAAA CTCCATGGGG ATTAACATTT      660

AATTTTGATG ATAGGGGATG TGATCAAGTT AGAAAATTCA TTTTAGAAAA TGTCGAGTAT      720

TGGTTTAAGA CCTTTAAAAT CGATGGTCTG AGACTGGATG CAGTTCATGC AATTTTTGAT      780

AATTCGCCTA AGCATATCCT CCAAGAGATC GCTGAAAAAG CCCATCAATT AGGAAAATTT      840

GTTATTGCTG AAAGTGATTT AAATGATCCA AAAATAGTAA AAGATGATTG TGGATATAAA      900

ATAGATGCTC AATGGGTTGA CGATTTCCAC CACGCAGTTC ATGCATTCAT AACCAAAGAA      960

AAAGATTATT ATTACCAGGA TTTTGGAAGG ATAGAAGATA TAGAGAAAAC TTTTAAAGAT     1020

GTTTTTGTTT ATGATGGAAA GTATTCTAGA TACAGAGGAA GAACTCATGG TGCTCCTGTA     1080
```

-continued

```
GGTGATCTTC CACCACGTAA ATTTGTAGTC TTCATACAAA ATCACGATCA AGTAGGAAAT    1140

AGAGGAAATG GGGAAAGACT TTCCATATTA ACCGATAAAA CGACATACCT TATGGCAGCC    1200

ACACTATATA TACTCTCACC GTATATACCG CTAATATTTA TGGGCGAGGA ATATTATGAG    1260

ACGAATCCTT TTTTCTTCTT CTCTGATTTC TCAGATCCCG TATTAATTAA GGGTGTTAGA    1320

GAAGGTAGAC TAAAGGAAAA TAATCAAATG ATAGATCCAC AATCTGAGGA AGCGTTCTTA    1380

AAGAGTAAAC TTTCATGGAA AATTGATGAG GAAGTTTTAG ATTATTATAA ACAACTGATA    1440

AATATCAGAA AGAGATATAA TAATTGTAAA AGGGTAAAGG AAGTTAGGAG AGAAGGGAAC    1500

TGTATTACTT TGATCATGGA AAAAATAGGA ATAATTGCAT CGTTTGATGA TATTGTAATT    1560

AATTCTAAAA TTACAGGTAA TTTACTTATA GGCATAGGAT TTCCGAAAAA ATTGAAAAAA    1620

GATGAATTAA TTAAGGTTAA CAGAGGTGTT GGGGTATATC AATTAGAA               1668
```

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Phe Ser Phe Gly Gly Asn Ile Glu Lys Asn Lys Gly Ile Phe Lys
1               5                   10                  15

Leu Trp Ala Pro Tyr Val Asn Ser Val Lys Leu Lys Leu Ser
            20                  25                  30
```

(2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Ile Asp Ala Gln Trp Val Asp Asp Phe His His Ala Val His Ala Phe
1               5                   10                  15

Ile Thr Lys
```

(2) INFORMATION FOR SEQ ID NO:5:

(i) SEQUENCE CHARACTERISTICS:
        (A) LENGTH: 1668 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
ATG TTT TCG TTC GGT GGA AAT ATT GAA AAA AAT AAA GGT ATC TTT AAG       48
Met Phe Ser Phe Gly Gly Asn Ile Glu Lys Asn Lys Gly Ile Phe Lys
 1               5                  10                  15

TTA TGG GCA CCT TAT GTT AAT AGT GTT AAG CTG AAG TTA AGC AAA AAA       96
Leu Trp Ala Pro Tyr Val Asn Ser Val Lys Leu Lys Leu Ser Lys Lys
            20                  25                  30
```

```
CTT ATT CCA ATG GAA AAA AAC GAT GAG GGA TTT TTC GAA GTA GAA ATA      144
Leu Ile Pro Met Glu Lys Asn Asp Glu Gly Phe Phe Glu Val Glu Ile
        35                  40                  45

GAC GAT ATC GAG GAA AAT TTA ACC TAT TCT TAT ATT ATA GAA GAT AAG      192
Asp Asp Ile Glu Glu Asn Leu Thr Tyr Ser Tyr Ile Ile Glu Asp Lys
 50                  55                  60

AGA GAG ATA CCT GAT CCC GCA TCA CGA TAT CAA CCT TTA GGA GTT CAT      240
Arg Glu Ile Pro Asp Pro Ala Ser Arg Tyr Gln Pro Leu Gly Val His
 65                  70                  75                  80

GAC AAA TCA CAA CTT ATA AGA ACA GAT TAT CAG ATT CTT GAC CTT GGA      288
Asp Lys Ser Gln Leu Ile Arg Thr Asp Tyr Gln Ile Leu Asp Leu Gly
                 85                  90                  95

AAA GTA AAA ATA GAA GAT CTA ATA ATA TAT GAA CTC CAC GTT GGT ACT      336
Lys Val Lys Ile Glu Asp Leu Ile Ile Tyr Glu Leu His Val Gly Thr
             100                 105                 110

TTT TCC CAA GAA GGA AAT TTC AAA GGA GTA ATA GAA AAG TTA GAT TAC      384
Phe Ser Gln Glu Gly Asn Phe Lys Gly Val Ile Glu Lys Leu Asp Tyr
         115                 120                 125

CTC AAG GAT CTA GGA ATC ACA GGA ATT GAA CTG ATG CCT GTG GCA CAA      432
Leu Lys Asp Leu Gly Ile Thr Gly Ile Glu Leu Met Pro Val Ala Gln
    130                 135                 140

TTT CCA GGG AAT AGA GAT TGG GGA TAC GAT GGT GTT TTT CTA TAC GCA      480
Phe Pro Gly Asn Arg Asp Trp Gly Tyr Asp Gly Val Phe Leu Tyr Ala
145                 150                 155                 160

GTT CAA AAT ACT TAT GGC GGA CCA TGG GAA TTG GCT AAG CTA GTA AAC      528
Val Gln Asn Thr Tyr Gly Gly Pro Trp Glu Leu Ala Lys Leu Val Asn
                165                 170                 175

GAG GCA CAT AAA AGG GGA ATA GCC GTA ATT TTG GAT GTT GTA TAT AAT      576
Glu Ala His Lys Arg Gly Ile Ala Val Ile Leu Asp Val Val Tyr Asn
            180                 185                 190

CAT ATA GGT CCT GAG GGA AAT TAC CTT TTA GGA TTA GGT CCT TAT TTT      624
His Ile Gly Pro Glu Gly Asn Tyr Leu Leu Gly Leu Gly Pro Tyr Phe
        195                 200                 205

TCA GAC AGA TAT AAA ACT CCA TGG GGA TTA ACA TTT AAT TTT GAT GAT      672
Ser Asp Arg Tyr Lys Thr Pro Trp Gly Leu Thr Phe Asn Phe Asp Asp
    210                 215                 220

AGG GGA TGT GAT CAA GTT AGA AAA TTC ATT TTA GAA AAT GTC GAG TAT      720
Arg Gly Cys Asp Gln Val Arg Lys Phe Ile Leu Glu Asn Val Glu Tyr
225                 230                 235                 240

TGG TTT AAG ACC TTT AAA ATC GAT GGT CTG AGA CTG GAT GCA GTT CAT      768
Trp Phe Lys Thr Phe Lys Ile Asp Gly Leu Arg Leu Asp Ala Val His
                245                 250                 255

GCA ATT TTT GAT AAT TCG CCT AAG CAT ATC CTC CAA GAG ATC GCT GAA      816
Ala Ile Phe Asp Asn Ser Pro Lys His Ile Leu Gln Glu Ile Ala Glu
            260                 265                 270

AAA GCC CAT CAA TTA GGA AAA TTT GTT ATT GCT GAA AGT GAT TTA AAT      864
Lys Ala His Gln Leu Gly Lys Phe Val Ile Ala Glu Ser Asp Leu Asn
        275                 280                 285

GAT CCA AAA ATA GTA AAA GAT GAT TGT GGA TAT AAA ATA GAT GCT CAA      912
Asp Pro Lys Ile Val Lys Asp Asp Cys Gly Tyr Lys Ile Asp Ala Gln
    290                 295                 300

TGG GTT GAC GAT TTC CAC CAC GCA GTT CAT GCA TTC ATA ACC AAA GAA      960
Trp Val Asp Asp Phe His His Ala Val His Ala Phe Ile Thr Lys Glu
305                 310                 315                 320

AAA GAT TAT TAT TAC CAG GAT TTT GGA AGG ATA GAA GAT ATA GAG AAA     1008
Lys Asp Tyr Tyr Tyr Gln Asp Phe Gly Arg Ile Glu Asp Ile Glu Lys
                325                 330                 335

ACT TTT AAA GAT GTT TTT GTT TAT GAT GGA AAG TAT TCT AGA TAC AGA     1056
Thr Phe Lys Asp Val Phe Val Tyr Asp Gly Lys Tyr Ser Arg Tyr Arg
            340                 345                 350
```

```
GGA AGA ACT CAT GGT GCT CCT GTA GGT GAT CTT CCA CCA CGT AAA TTT    1104
Gly Arg Thr His Gly Ala Pro Val Gly Asp Leu Pro Pro Arg Lys Phe
        355                 360                 365

GTA GTC TTC ATA CAA AAT CAC GAT CAA GTA GGA AAT AGA GGA AAT GGG    1152
Val Val Phe Ile Gln Asn His Asp Gln Val Gly Asn Arg Gly Asn Gly
        370                 375                 380

GAA AGA CTT TCC ATA TTA ACC GAT AAA ACG ACA TAC CTT ATG GCA GCC    1200
Glu Arg Leu Ser Ile Leu Thr Asp Lys Thr Thr Tyr Leu Met Ala Ala
385                 390                 395                 400

ACA CTA TAT ATA CTC TCA CCG TAT ATA CCG CTA ATA TTT ATG GGC GAG    1248
Thr Leu Tyr Ile Leu Ser Pro Tyr Ile Pro Leu Ile Phe Met Gly Glu
                405                 410                 415

GAA TAT TAT GAG ACG AAT CCT TTT TTC TTC TTC TCT GAT TTC TCA GAT    1296
Glu Tyr Tyr Glu Thr Asn Pro Phe Phe Phe Phe Ser Asp Phe Ser Asp
            420                 425                 430

CCC GTA TTA ATT AAG GGT GTT AGA GAA GGT AGA CTA AAG GAA AAT AAT    1344
Pro Val Leu Ile Lys Gly Val Arg Glu Gly Arg Leu Lys Glu Asn Asn
                435                 440                 445

CAA ATG ATA GAT CCA CAA TCT GAG GAA GCG TTC TTA AAG AGT AAA CTT    1392
Gln Met Ile Asp Pro Gln Ser Glu Glu Ala Phe Leu Lys Ser Lys Leu
        450                 455                 460

TCA TGG AAA ATT GAT GAG GAA GTT TTA GAT TAT TAT AAA CAA CTG ATA    1440
Ser Trp Lys Ile Asp Glu Glu Val Leu Asp Tyr Tyr Lys Gln Leu Ile
465                 470                 475                 480

AAT ATC AGA AAG AGA TAT AAT AAT TGT AAA AGG GTA AAG GAA GTT AGG    1488
Asn Ile Arg Lys Arg Tyr Asn Asn Cys Lys Arg Val Lys Glu Val Arg
                485                 490                 495

AGA GAA GGG AAC TGT ATT ACT TTG ATC ATG GAA AAA ATA GGA ATA ATT    1536
Arg Glu Gly Asn Cys Ile Thr Leu Ile Met Glu Lys Ile Gly Ile Ile
                500                 505                 510

GCA TCG TTT GAT GAT ATT GTA ATT AAT TCT AAA ATT ACA GGT AAT TTA    1584
Ala Ser Phe Asp Asp Ile Val Ile Asn Ser Lys Ile Thr Gly Asn Leu
        515                 520                 525

CTT ATA GGC ATA GGA TTT CCG AAA AAA TTG AAA AAA GAT GAA TTA ATT    1632
Leu Ile Gly Ile Gly Phe Pro Lys Lys Leu Lys Lys Asp Glu Leu Ile
        530                 535                 540

AAG GTT AAC AGA GGT GTT GGG GTA TAT CAA TTA GAA                    1668
Lys Val Asn Arg Gly Val Gly Val Tyr Gln Leu Glu
545                 550                 555
```

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CTGCAGTTTT TTAATAAAAT CAGGAGGAAA AAAT                              34
```

(2) INFORMATION FOR SEQ ID NO:7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA

```
    (xi) SEQUENCE DESCRIPTION: SEQ ID NO:7:

TGAAGCTTGA GCT                                                              13

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

TTYAARYTNT GGGCNCC                                                          17

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CARTGGGTNG AYGAYTTYCA                                                       20

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GTAAAACGAC GGCCAGT                                                          17

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CTGCAGTTTT TTAATAAAAT CAGGAGGA                                              28

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

AAAAATATGT TTTCGTTCGG TGGAAAT                                               27
```

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ATTTCCACCG AACGAAAA                                              18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CATATTTTTT CCTCCTGA                                              18

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TTTTATTAAA AAACTGCAG                                          19

(2) INFORMATION FOR SEQ ID NO:16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

AACAGAGGTG TTGGG                                                15

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GTATATCAAT TAGAATGAAG CTTGAGCT                                28

-continued (2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CAAGCTTCAT TCTA                    14

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

ATTGATATAC CCCAACACCT CTGTT          25

RECOMBINANT THERMOSTABLE ENZYME WHICH RELEASES TREHALOSE FROM NON-REDUCING SACCHARIDE

CROSS-REFERENCE TO RELATED APPLICATIONS

This is a continuation of application Ser. No. 08/798,269 filed Feb. 11, 1997, which is a division of application Ser. No. 08/505,377, filed Jul. 21, 1995, U.S. Pat. No. 5,856,146 the entire contents of both applications are herein incorporated by reference.

BACKGROUND OF THE INVENTION

1. Field of the Invention

The present invention relates to a recombinant thermostable enzyme which releases trehalose from non-reducing saccharides having a trehalose structure as an end unit and a degree of glucose polymerization of at least 3.

2. Description of the Prior Art

Trehalose is a disaccharide which consists of 2 glucose molecules that are linked together with their reducing groups, and, naturally, it is present in fungi, algae, insects, etc., in an extremely small quantity. Having no reducing residue within the molecule, trehalose does not cause an unsatisfactory browning reaction even when heated in the presence of amino acids or the like, and because of this it can advantageously sweeten food products without fear of causing unsatisfactory coloration and deterioration. Trehalose, however, could not have been readily prepared in a desired amount by conventional production methods, so that it has not scarcely been used for sweetening food products.

Conventional production methods are roughly classified into 2 groups, i.e. the one using cells of microorganisms and the other using a multi-enzymatic system where several enzymes are allowed to act on saccharides. The former, as disclosed in Japanese Patent Laid-Open No.154,485/75, is a method which comprises growing microorganisms such as bacteria and yeasts in nutrient culture media, and collecting trehalose mainly from the proliferated cells. The latter, as disclosed in Japanese Patent Laid-Open No.216,695/83, is a method which comprises providing maltose as a substrate, allowing a multi-enzymatic system using maltose- and trehalose-phosphorylases to act on maltose, and recovering the formed trehalose from the reaction system. The former facilitates the growth of microorganisms, but has a demerit that the content in the microorganisms is at most 15 w/w %, on a dry solid basis (d.s.b.). Although the latter can readily separate trehalose, it is theoretically difficult to increase the trehalose yield by allowing such phosphorylases to act on substrates at a considerably-high concentration because the enzymatic reaction in itself is an equilibrium reaction of 2 different types of enzymes and the equilibrium point constantly inclines to the side of forming glucose phosphate.

In view of the foregoing, the present inventors energetically screened enzymes which form saccharides having a trehalose structure from amylaceous saccharides, and have found that microorganisms such as those of the genera Rhizobium and Arthrobacter produce an absolutely novel enzyme which forms non-reducing saccharides having a trehalose structure as an end unit from reducing amylaceous saccharides having a degree of glucose polymerization of at least 3. They disclosed such an enzyme in Japanese Patent Application No.349,216/93. At almost the same time, they also found that these non-reducing saccharides are nearly quantitatively hydrolyzed into trehalose and glucose and/or maltooligosaccharides by other enzymes produced from the same microorganisms of the genera Rhizobium and Arthrobacter.

It was found that the enzymes produced from the aforesaid microorganisms have an optimum temperature of about 40° C., and have some difficulties in their thermostability when actually used to produce trehalose. It is recognized in this field that a recommendable temperature in the saccharification reaction of starch or amylaceous saccharides is one which exceeds 55° C. because bacterial contamination will occur at a temperature of 55° C. or lower and decreasing the pH of the reaction mixtures and inactivating the enzymes used. Thus, a relatively-large amount of substrates remain intact. While the use of enzymes with a poor thermostability, a great care should be taken to control the pH, and, when the pH level lowers to an extremely low level, alkalis should be added to reaction mixtures to increase the pH level as quickly as possible.

In view of the foregoing, the present inventors screened thermostable enzyme with a satisfactory activity and have found that enzymes produced from microorganisms of the genus Sulfolobus including *Sulfolobus acidocaldarius* (ATCC 33909) are not substantially inactivated even when incubated at a temperature exceeding 55° C., and they efficiently release trehalose from non-reducing saccharides having a trehalose structure as an end unit and a degree of glucose polymerization of at least 3. These microorganisms, however, are not sufficient in the enzyme productivity, and this requires a relatively-large scale culture to industrially produce trehalose from those non-reducing saccharides.

Recently, the recombinant DNA technology has made a remarkable progress. At present, even an enzyme whose total amino acid sequence has not been revealed can be readily prepared in a desired amount, if once a gene encoding the enzyme is isolated and the base sequence is decoded, by preparing a recombinant DNA containing a DNA that encodes the enzyme, introducing the recombinant DNA into microorganisms or cells of plants or animals, and culturing the resultant transformants. Under these circumstances, urgently required are to find a gene that encodes the thermostable enzyme and to decode the base sequence.

SUMMARY OF THE INVENTION

It is an object of the present invention to provide a recombinant thermostable enzyme which releases trehalose from non-reducing saccharides having a trehalose structure as an end unit and a degree of glucose polymerization of at least 3 by using the recombinant DNA technology.

It is a further object of the present invention to provide a DNA which encodes the recombinant thermostable enzyme.

It is yet another object of the present invention to provide a replicable recombinant DNA which contains the DNA.

It is another object of the present invention to provide a transformant into which the recombinant DNA is introduced.

It is yet another object of the present invention to provide a process for preparing the recombinant thermostable enzyme using the transformant.

It is another object of the present invention to provide an enzymatic conversion method for releasing trehalose from non-reducing saccharides having a trehalose structure as an end unit and a degree of glucose polymerization of at least 3.

The first object of the present invention is attained by a recombinant thermostable enzyme having the following physicochemical properties:

(1) Action
   Releasing trehalose from non-reducing saccharides having a trehalose structure as an end unit and a degree of glucose polymerization of at least 3;
(2) Molecular weight
   About 54,000–64,000 daltons on sodium dodecyl sulfate polyacrylamide gel electrophoresis (SDS-PAGE);
(3) Isoelectric point (pI)
   About 5.6–6.6 on isoelectrophoresis; and
(4) Thermostability
   Substantially not inactivated even when incubated in an aqueous solution (pH 7.0) at 85° C. for 60 min.

The second object of the present invention is attained by a DNA which encodes the recombinant thermostable enzyme.

The third object of the present invention is attained by a replicable recombinant DNA which contains a self-replicable vector and the recombinant thermostable enzyme.

The fourth object of the present invention is attained by a transformant which is prepared by introducing the replicable recombinant DNA into an appropriate host.

The fifth object of the present invention is attained by a process for preparing the recombinant thermostable enzyme which comprises culturing the transformant in a nutrient culture medium, and collecting the formed recombinant thermostable enzyme from the culture.

The sixth object of the present invention is attained by an enzymatic conversion method of non-reducing saccharides having a trehalose structure as an end unit and a degree of glucose polymerization of at least 3, which contains a step of allowing the recombinant thermostable enzyme to act on the non-reducing saccharides to release trehalose.

BRIEF DESCRIPTION OF THE ACCOMPANYING DRAWINGS

DETAILED DESCRIPTION OF THE INVENTION

Figure 1:
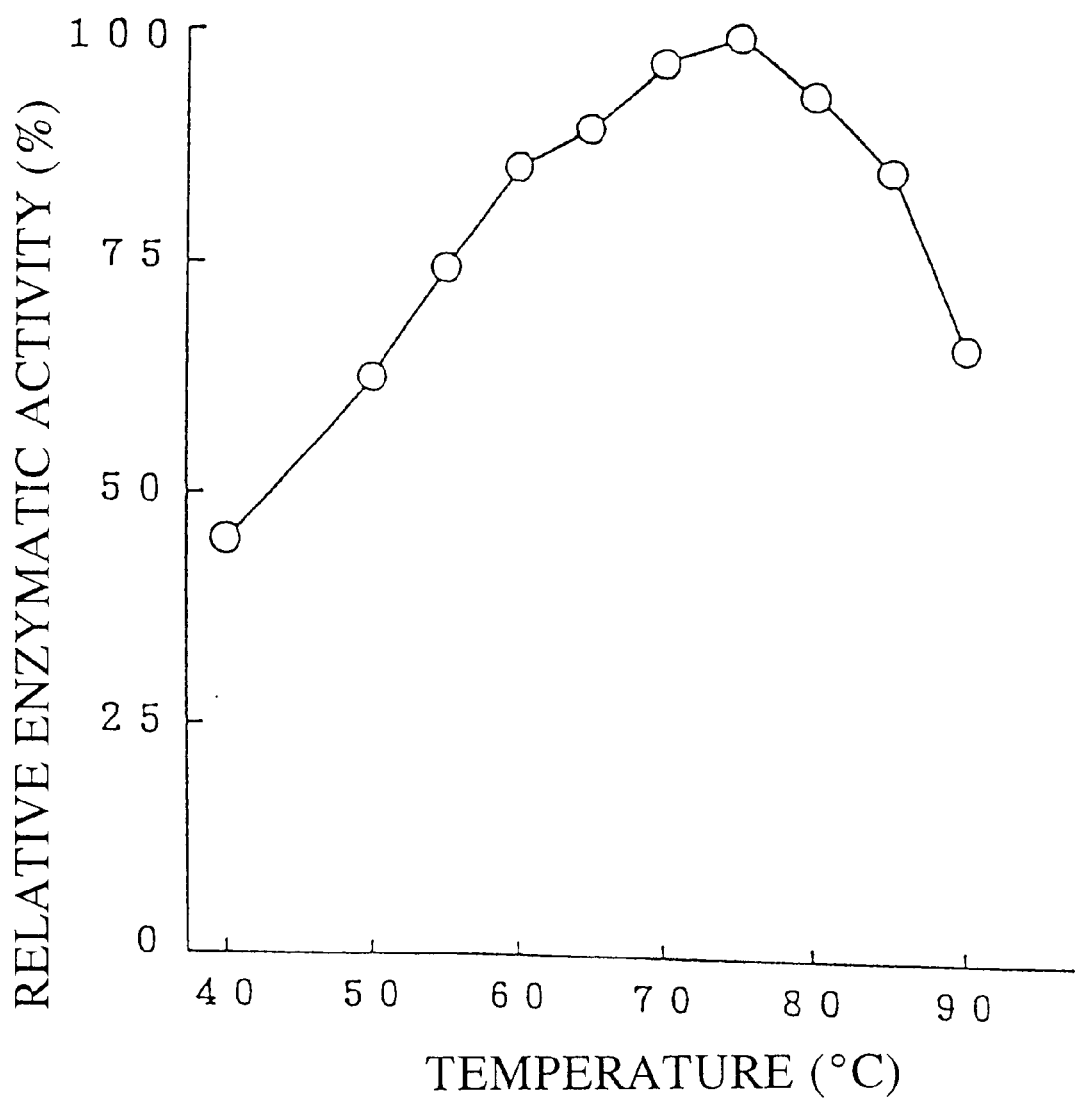
FIG. 1 is a figure of the optimum temperature of a thermostable enzyme produced from *Sulfolobus acidocaldarius* (ATCC 33909).

The recombinant thermostable enzyme according to the present invention releases trehalose from non-reducing saccharides having a trehalose structure as an end unit and a degree of glucose polymerization of at least 3 without substantial inactivation even when allowed to react at a temperature exceeding 55° C.

The DNA according to the present invention expresses the production of the present enzyme by introducing the DNA into an appropriate self-replicable vector to form a replicable recombinant DNA, and introducing the replicable recombinant DNA into an appropriate host which does not produce the present enzyme in itself but readily proliferates.

The recombinant DNA according to the present invention expresses the production of the present enzyme by introducing it into an appropriate host which does not produce the present enzyme but readily proliferates.

The transformant according to the present invention produces the present enzyme when cultured.

Culturing of the transformant by the present process facilitates the production of the present enzyme in a desired amount.

According to the present enzymatic conversion method converts non-reducing saccharides having a trehalose structure as an end unit and a degree of glucose polymerization of at least 3 into saccharide compositions containing trehalose and glucose and/or maltooligosaccharides.

The present invention has been made based on the finding of a novel enzyme which releases trehalose from non-reducing saccharides having a trehalose structure as an end unit and a degree of glucose polymerization of at least 3. Such an enzyme is obtainable from cultures of microorganisms of the species *Sulfolobus acidocaldarius* (ATCC 33909). The present inventors isolated such an enzyme by using in combination a various purification methods comprising column chromatography as a main technique, studied their properties and features, and revealed that the reality is a polypeptide with the following physicochemical properties:

(1) Action
   Releasing trehalose from non-reducing saccharides having a trehalose structure as an end unit and a degree of glucose polymerization of at least 3;
(2) Molecular weight
   About 54,000–64,000 daltons on sodium dodecyl sulfate polyacrylamide gel electrophoresis (SDS-PAGE);
(3) Isoelectric point (pI)
   About 5.6–6.6 on isoelectrophoresis; and
(4) Optimum temperature
   Exhibiting an optimum temperature of about 75° C. when incubated at a pH 6.0 for 30 min;
(5) Optimum pH
   Exhibiting an optimum pH of about 5.5–6.0 when incubated at 60° C. for 30 min;
(6) Thermostability
   Stable up to a temperature of about 85° C. even when incubated at a pH 7.0 for 60 min; and
(7) pH Stability
   Stable up to a pH of about 5.5–9.5 when incubated at 25° C. for 16 hours.

The followings are the explanations of the experiments conducted to reveal the physicochemical properties of a thermostable enzyme produced from *Sulfolobus acidocaldarius* (ATCC 33909):

Experiment 1
Preparation of Purified Enzyme

Into 500-ml flasks were poured 100 ml aliquots of a liquid culture medium containing 0.1 w/v % polypeptone, 0.1 w/v % yeast extract, 0.2 w/v % ammonium sulfate, 0.05 w/v % potassium dihydrogen phosphate, 0.02 w/v % magnesium sulfate heptahydrate, 0.02 w/v % potassium chloride, and water, and the flasks were sterilized by autoclaving at 120° C. for 20 min. After cooling the flasks a seed culture of *Sulfolobus acidocaldarius* (ATCC 33909) was inoculated into each liquid culture medium in each flask, followed by the incubation at 75° C. for 24 hours under a rotary shaking condition of 130 rpm to obtain a first seed culture. About 5 L of a fresh preparation of the same liquid culture medium was poured into a 10-L fermenter, sterilized similarly as above, cooled to 75° C., and adjusted to a pH 3.0, followed by inoculating one v/v % of the first seed culture into the sterilized liquid culture medium in the fermenter, and culturing the microorganisms at 75° C. for 24 hours under an aeration condition of 500 ml/min. Thereafter, about 250 L of a fresh preparation of the same liquid culture medium was poured into a 300-L fermenter, sterilized similarly as above, cooled to 75° C., and adjusted to a pH 3.0, followed by inoculating one v/v % of the second seed culture into the sterilized liquid culture medium, and culturing the microorganisms at 75° C. for 42 hours under an aeration condition of 100 L/min.

About 170 L of the resultant culture was filtered with an SF membrane, and the filtrate was centrifuged to obtain wet cells. About 258 g of the wet cells was suspended in 300 ml of 10 mM phosphate buffer (pH 7.0) and ultrasonicated to disrupt them. The cell debris thus obtained was centrifuged at 10,000 rpm for 30 min, and about 300 ml of the resultant supernatant was mixed with ammonium sulfate to give a saturation degree of 70 w/v %, allowed to stand at 4° C. for 24 hours, and centrifuged at 10,000 rpm for 30 min. The precipitate was collected, dissolved in an adequate amount of 10 mM Tris-HCl buffer (pH 8.5), and dialyzed against a fresh preparation of the same buffer for 24 hours. Thereafter, the dialyzed solution was centrifuged at 10,000 rpm for 30 min to obtain an about 300 ml of a supernatant with an enzymatic activity.

The supernatant was fed to a column packed with about 360 ml of "DEAE-TOYOPEARL®", a gel for ion-exchange column chromatography commercialized by Tosoh Corporation, Tokyo, Japan, and fed with a linear gradient buffer raging from 0 M to 0.3 M in 10 mM Tris-HCl buffer (pH 8.5). Fractions with an enzymatic activity, eluted at a concentration of about 0.1 M sodium chloride, were collected, pooled, and dialyzed for 10 hours against 10 mM Tris-HCl buffer (pH 8.5) containing one M ammonium sulfate. The dialyzed solution was centrifuged to remove insoluble substances, fed to a column packed with about 350 ml of "BUTYL-TOYOPEARL® 650", a gel for hydrophobic chromatography commercialized by Tosoh Corporation, Tokyo, Japan, which had been previously equilibrated with 10 mM Tris-HCl buffer (pH 8.5) containing one M ammonium sulfate, and fed with a linear gradient buffer ranging from 1 M to 0 M ammonium sulfate in 10 mM Tris-HCl buffer (pH 8.5).

Fractions with an enzymatic activity eluted at about 0.2 M ammonium sulfate were collected, pooled, dialyzed for 16 hours against 10 mM Tris-HCl buffer (pH 8.5) containing 0.2 M sodium chloride, and centrifuged to remove insoluble substances. The resultant supernatant was fed to a column packed with about 350 ml of "TOYOPEARL® HW-55", a gel for gel chromatography commercialized by Sepracor, Massachusetts, USA, which had been previously equilibrated with 10 mM Tris-HCl buffer (pH 8.5) containing 0.2 M sodium chloride. Fractions with an enzymatic activity were collected from the eluate, pooled, and dialyzed against 10 mM Tris-HCl buffer (pH 8.5) for 16 hours. The dialyzed solution was centrifuged to remove insoluble substances, and the supernatant was fed to a column packed with about 10 ml of "SUPERROSE 12 HR 10/30", a product of Pharmacia LKB Uppsala, Sweden, which had been previously equilibrated with 10 mM Tris-HCl buffer (pH 8.5), and eluted with 10 mM Tris-HCl buffer (pH 8.5). Fractions with an enzymatic activity eluted at about 0.1 M sodium chloride were collected and pooled for use in the following experiments. The purified enzyme thus obtained had a specific activity of about 378 units/mg protein, and the yield was about 0.86 units per one L of the culture.

The purified protein was in usual manner electrophoresed in 7.5 w/v % polyacrylamide gel to find a substantially single protein band with an enzymatic activity. This indicated that the purified protein was extremely pure.

Throughout the specification the activity of the present thermostable enzyme is expressed by the value measured on the following assay: Place 4 ml of 50 mM phosphate buffer (pH 6.0) containing as a substrate 1.25 w/v % α-maltotriosyltrehalose in a test tube, add one ml of an adequately diluted enzyme solution to the test tube, and incubate the mixture solution at 60° C. for 30 min to effect enzymatic reaction. Thereafter, one ml of the reaction mixture is mixed with 2 ml of the Somogyi copper solution to suspend the enzymatic reaction, followed by assaying the reducing power on the Somogyi-Nelson's method. As a control, a system using an enzyme solution, which has been heated at 100° C. for 30 min to inactivate the enzyme, is provided and similarly treated as above. One unit activity of the thermostable enzyme is defined as the amount of enzyme which increases the reducing power of one μmol glucose per min under the same conditions as mentioned above.

Experiment 2
Physicochemical Property of Thermostable Enzyme

Experiment 2-1
Action α-Glucosyltrehalose, α-maltosyltrehalose, α-maltotriosyltrehalose, α-maltotetraosyltrehalose or α-maltopentaosyltrehalose as a substrate was dissolved in 50 mM acetate buffer (pH 5.5) into a 20 w/v % solution which was then admixed with 2 units/g substrate, d.s.b., of the purified thermostable enzyme in Experiment 1, and subjected to an enzymatic reaction at 60° C. for 48 hours. The reaction mixture was desalted in usual manner, and the saccharide composition of the resultant solution was analyzed on high-performance liquid chromatography (HPLC) using a column of "WAKOBEADS WB-T-330", a column for HPLC commercialized by Wako Pure Chemical Industries, Ltd., Tokyo, Japan. The HPLC procedure was carried out at ambient temperature, and water was used as an eluant and fed to the column at a flow rate of 0.5 ml/min while monitoring the eluate on "MODEL RI-8012", a differential refractometer commercialized by Tosoh Corporation, Tokyo, Japan. As a control, 5 systems using as a substrate maltotriose, maltotetraose, maltopentaose, maltohexaose and maltoheptaose were respectively provided, and similarly treated as above. The results were in Table 1.

TABLE 1

| Substrate | Saccharide in reaction mixture | Elution time on HPLC (min) | Composition (%) |
| --- | --- | --- | --- |
| α-Glucosyltrehalose | Trehalose | 27.4 | 7.2 |
| | Glucose | 33.8 | 3.9 |
| | α-Glucosyltrehalose | 23.3 | 88.9 |
| α-Maltosyltrehalose | Trehalose | 27.4 | 40.2 |
| | Maltose | 28.7 | 40.5 |
| | α-Maltosyltrehalose | 21.6 | 19.3 |
| α-Maltotriosyltrehalose | Trehalose | 27.4 | 41.1 |
| | Maltotriose | 25.9 | 58.2 |
| | α-Maltotriosyltrehalose | 19.7 | 0.7 |

TABLE 1-continued

| Substrate | Saccharide in reaction mixture | Elution time on HPLC (min) | Composition (%) |
|---|---|---|---|
| α-Maltotetraosyl-trehalose | Trehalose | 27.4 | 34.0 |
| | Maltotetraose | 24.1 | 65.8 |
| | α-Maltotetraosyl-trehalose | 18.7 | 0.2 |
| α-Maltopentaosyl-trehalose | Trehalose | 27.4 | 29.1 |
| | Maltopentaose | 22.6 | 70.6 |
| | α-Maltopentaosyl-trehalose | 17.8 | 0.3 |
| Maltotriose | Maltotriose | 25.9 | 100 |
| Maltotetraose | Maltotetraose | 24.1 | 100 |
| Maltopentaose | Maltopentaose | 22.6 | 100 |
| Maltohexaose | Maltohexaose | 21.8 | 100 |
| Maltoheptaose | Maltoheptaose | 21.0 | 100 |

The results in Table 1 show that the purified enzyme nearly quantitatively releases trehalose and glucose or maltooligosaccharides from non-reducing saccharides having a trehalose structure as an end unit and a degree of glucose polymerization of at least 3, but does not substantially act on maltooligosaccharides having a degree of glucose polymerization of at least 3. These facts indicate that the purified enzyme specifically acts on non-reducing saccharides having a trehalose structure as an end unit and a degree of glucose polymerization of at least 3, and specifically hydrolyzes the glycosidic linkages between trehalose- and glycosyl-residues. Such an enzyme has not been reported and it can be estimated to have a novel enzymatic pathway.

Experiment 2-2
Molecular Weight

In accordance with the method reported by U. K. Laemmli in *Nature*, Vol.227, pp.680–685 (1970), the purified enzyme in Experiment 1 was electrophoresed on SDS-PAGE to give a single protein band with an enzymatic activity at a position corresponding to about 54,000–64,000 daltons. The marker proteins used in this experiment were myosin (MW=200,000 daltons), β-galactosidase (MW=116,250 daltons), phosphorylase B (MW=97,400 daltons), serum albumin (MW=66,200 daltons) and ovalbumin (MW=45,000 daltons).

Experiment 2-3
Isoelectric Point

The purified enzyme in Experiment 1 gave an isoelectric point of about 5.6–6.6 when isoelectrophoresed in a polyacrylamide gel containing 2 w/v % ampholine.

Experiment 2-4
Optimum Temperature

As is shown in FIG. 1, the optimum temperature of the purified enzyme in Experiment 1 was about 75° C. when incubated in usual manner in 20 mM phosphate buffer (pH 6.0) at different temperatures for 30 min.

Experiment 2-5
Optimum pH

Figure 2:
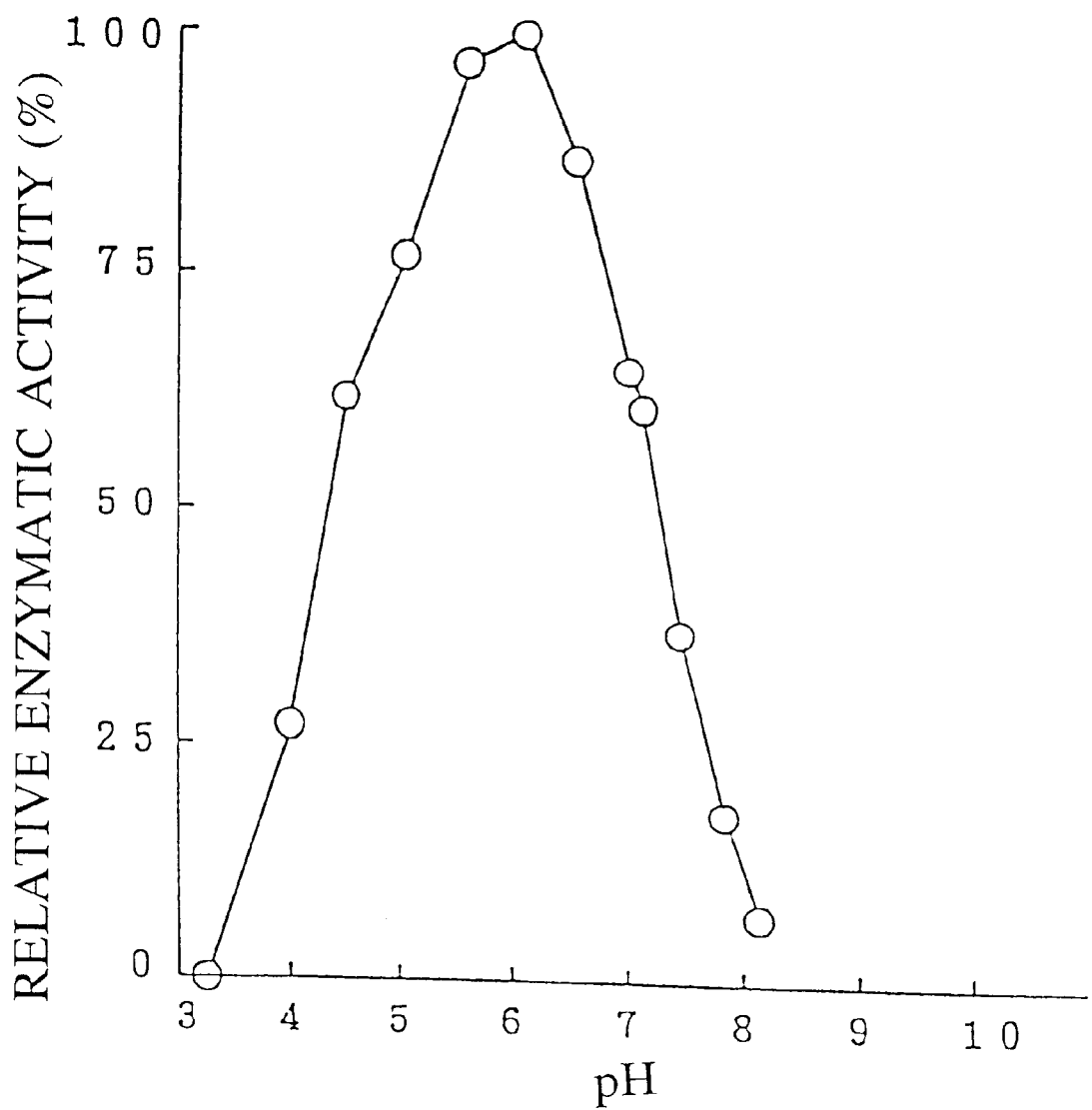
FIG. 2 is a figure of the optimum pH of a thermostable enzyme produced from *Sulfolobus acidocaldarius* (ATCC 33909).

As is shown in FIG. 2, the optimum pH of the purified-enzyme in Experiment 1 was about 5.5–6.0 when incubated in usual manner at 60° C. for 30 min in McIlvaine buffer with different pHs.

Experiment 2-6
Thermal Stability

Figure 3:
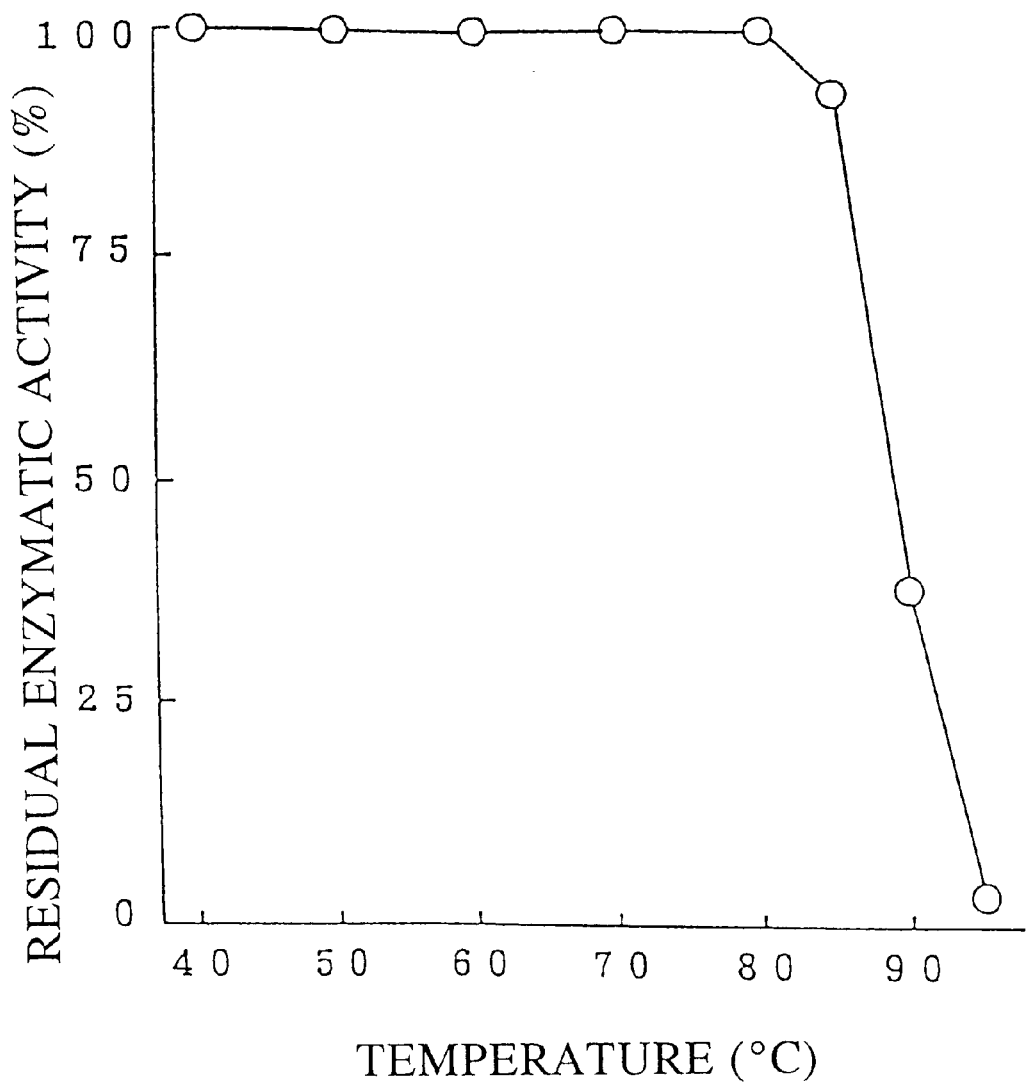
FIG. 3 is a figure of the thermostability of a thermostable enzyme produced from *Sulfolobus acidocaldarius* (ATCC 33909).

As is shown in FIG. 3, the purified enzyme in Experiment 1 was stable up to a temperature of about 85° C. when incubated in usual manner in 50 mM phosphate buffer (pH 7.0) for 60 min.

Experiment 2-7
pH Stability

Figure 4:
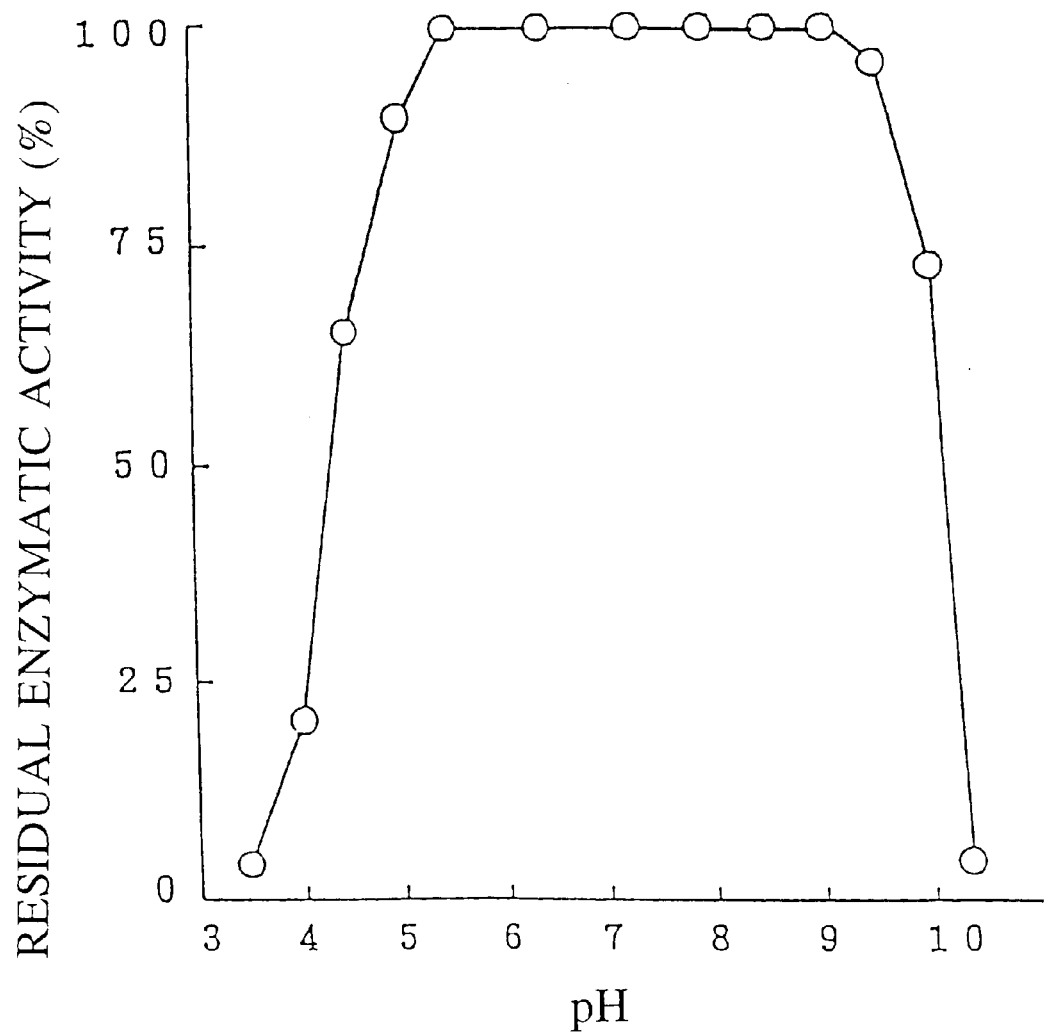
FIG. 4 is a figure of the pH stability of a thermostable enzyme produced from *Sulfolobus acidocaldarius* (ATCC 33909).
Figure 5:
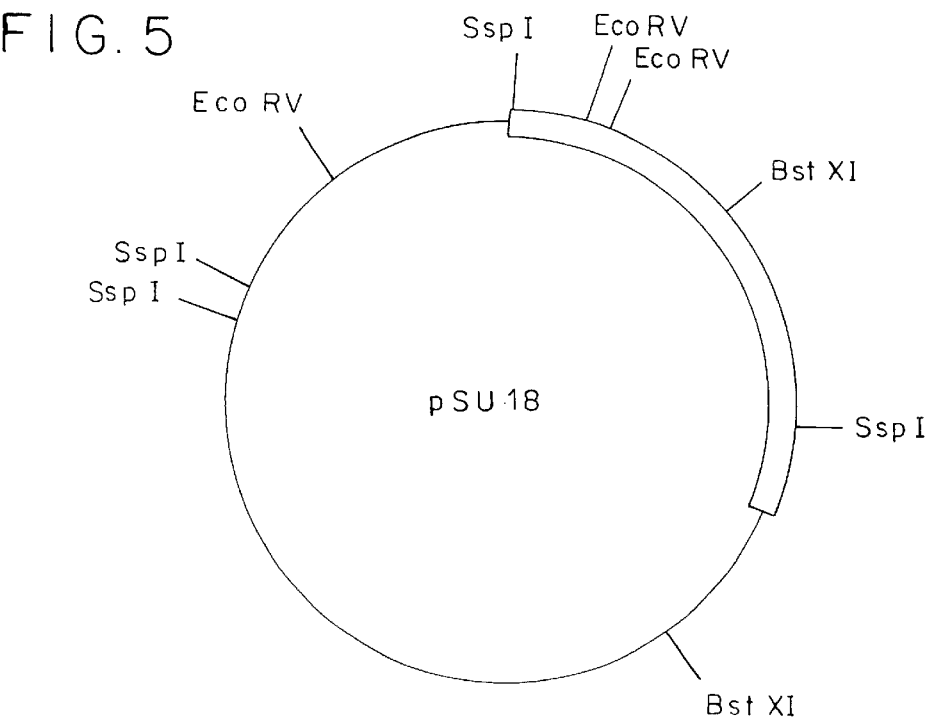
FIG. 5 is a restriction map of the recombinant DNA pSU18 according to the present invention.

As is shown in FIG. 4, the purified enzyme in Experiment 1 was stable at a pH in the range of about 5.5–9.5 when incubated in usual manner at 25° C. for 16 hours in McIlvaine buffer or 50 mM sodium carbonate/sodium hydrogen carbonate buffer with different pHs.

Experiment 2-8
Amino Acid Sequence Containing the N-terminal

The amino acid sequence containing the N-terminal of the purified enzyme in Experiment 1 was analyzed on "MODEL 473 A", a gas-phase protein sequencer commercialized by Perkin-Elmer Corp., Instrument Div., Norrwalk, USA, and revealing that it has the amino acid sequence in SEQ ID NO:3.

Experiment 2-9
Partial Amino Acid Sequence

An adequate amount of the purified enzyme in Experiment 1 was weighed, dialyzed against 10 mM Tris-HCl buffer (pH 9.0) at 4° C. for 18 hours, and admixed with 10 mM Tris-HCl buffer (pH 9.0) to give a concentration of about one mg/ml of the enzyme. About one ml of the resultant solution was placed in a container, admixed with 10 μg lysyl endopeptidase, and incubated at 30° C. for 64 hours to partially hydrolyze the enzyme. The resultant hydrolysate was applied to "μBONDAPAK C18", a column for HPLC commercialized by Japan Millipore Ltd., Tokyo, Japan, which had been previously equilibrated with 0.1 v/v % trifluoroacetate containing 8 v/v % aqueous acetonitrile, followed by feeding to the column 0.1 v/v % trifluoroacetate at a flow rate of 0.9 ml/min while increasing the concentration of aqueous acetonitrile from 8 to 48 v/v %, and collecting fractions containing a peptide fragment eluted about 57 min after the initiation of the feeding. The fractions were pooled, dried in vacuo, and dissolved in 0.1 v/v % trifluoroacetate containing 50 v/v % aqueous acetonitrile. Similarly as in Experiment 2–8, the peptide fragment was analyzed and revealed to have an amino acid sequence in SEQ ID NO:4.

Such an enzyme having these physicochemical properties has not been known and meaning that it is a novel enzyme.

A chromosomal DNA of *Sulfolobus acidocaldarius* (ATCC 33909) was screened by using an oligonucleotide as a probe which had been chemically synthesized based on the partial amino acid sequences in SEQ ID NOs:3 and 4, and this yielded a DNA fragment having a base sequence (SEQ ID NO:2.) from the 5'-terminus consisting of about 1,700 base pairs. The base sequence of the thermostable enzyme was decoded and revealing that it consists of 556 amino acids and has a partial amino acid sequence from the N-terminal in SEQ ID NO:1.

The sequential experimental steps used to reveal the amino acid sequence and the base sequence in SEQ ID NOs:1 to 2 are summarized in the below:

(1) A thermostable enzyme was isolated from a culture of a donor microorganism, highly purified, and determined for the N-terminal amino acid sequence. The purified enzyme was partially hydrolyzed with protease, and from which a peptide fragment was isolated and determined for amino acid sequence;

(2) A chromosomal DNA was isolated from a donor microorganism, purified and partially digested with a restriction enzyme to obtain a DNA fragment consisting of about 2,000–6,000 base pairs. The DNA fragment was ligated by DNA ligase to a plasmid vector, which had been previously cleaved with a restriction enzyme, to obtain a recombinant DNA;

(3) The recombinant DNA thus obtained was introduced into *Escherichia coli* to obtain transformants, and from which an objective transformant containing a DNA which encodes the objective enzyme was selected by the colony hybridization method using as a probe an oligonucleotide which had been chemically synthesized based on the above partial amino acid sequence; and (4) The recombinant DNA was obtained from the transformant and annealed with a primer, followed by allowing a DNA polymerase to act on the resultant to extend the primer, and determining the base sequence of the resultant complementary chain DNA by the dideoxy chain termination method. The comparison of an amino acid sequence, that could be estimated from the base sequence, with the aforesaid amino acid sequence confirmed that the base sequence encodes the enzyme.

The following Experiments 3 and 4 will concretely explain the above steps (2) to (4), and the techniques in themselves used therein are well known in this art, for example, those described by J. Sumbruck et al. in "*Molecular Cloning A Laboratory Manual*", 2nd edition, published by Cold Spring Harbor Laboratory Press, USA (1989).

Experiment 3
Preparation of Recombinant DNA Containing DNA which Encodes Thermostable Enzyme, and Transformant Obtained Therewith Experiment 3-1
Preparation of Chromosomal DNA To 500-ml flasks were placed about 100 ml aliquots of a liquid culture medium consisting of 0.1 w/v % polypeptone, 0.1 w/v % yeast extract, 0.2 w/v % ammonium sulfate, 0.05 w/v % potassium dihydrogen phosphate, 0.02 w/v % magnesium sulfate heptahydrate, 0.02 w/v % potassium chloride, and water, and the flasks were sterilized by autoclaving at 120° C. for 20 min, cooled, and adjusted to a pH 3.0 by the addition of sulfate. A seed culture of *Sulfolobus acidocaldarius* (ATCC 33909) was inoculated into each flask, incubated at 75° C. for 24 hours under a rotary shaking condition of 130 rpm to obtain a seed culture. About 5 L of a fresh preparation of the same liquid nutrient culture medium was placed in a 10-L fermenter, sterilized similarly as above, cooled to 75° C., adjusted to a pH 3.0, and inoculated with one v/v % of the seed culture, followed by the incubation at 75° C. for 24 hours under an aeration condition of 500 ml/min.

The resultant cells were collected by centrifugation, suspended in TES buffer (pH 8.0), admixed with 0.05 w/v % lysozyme, and incubated at 37° C. for 30 min. The resultant was freezed at −80° C. for one hour, admixed with TSS buffer (pH 9.0), heated to 60° C., and admixed with a mixture solution of TES buffer and phenol, and the resultant mixture was chilled with ice and centrifuged to obtain a supernatant. To the supernatant was added 2 fold volumes of cold ethanol to precipitate a crude chromosomal DNA which was then collected, dissolved in SSC buffer (pH 7.1), admixed with 7.5 µg ribonuclease and 125 µg protease, and incubated at 37° C. for one hour. Thereafter, a mixture solution of chloroform and isoamyl alcohol was added to the reaction mixture to extract the objective chromosomal DNA. The resultant extract was admixed with cold ethanol, followed by collecting the formed sediment containing a chromosomal DNA. The chromosomal DNA thus purified was dissolved in SSC buffer (pH 7.1) to give a concentration of about one mg/ml, and the solution was freezed at −80° C.

Experiment 3-2
Preparation of Recombinant DNA pSU18 and Transformant SU18

One ml of the purified chromosomal DNA in Experiment 3-1 was placed in a container, admixed with about 35 units of Sau 3AI, a restriction enzyme, and enzymatically reacted at 37° C. for 20 min to partially digest the chromosomal DNA, followed by recovering a DNA fragment consisting of about 2,000–6,000 base pairs by sucrose density-gradient ultracentrifugation. One µg of Bluescript II SK(+), a plasmid vector which is a colony-producing phagemid having a f1 origin of replication from the f1 filamentous phage that allows for rescue of the sense (+) DNA strand, a ColE1 origin of replication, an amplicillin resistance marker gene, and a T3 polymerase promoter linked to a lacZ gene by a polylinker with multiple cloning sites, and is commercialized by Stratagene Cloning Systems, California, USA, was weighed, subjected to the action of Bam HI, a restriction enzyme, to completely digest the plasmid vector, and admixed with 10 µg of the DNA fragment and 2 units of T4 DNA ligase. The mixture was allowed to stand at 4° C. overnight to ligate the DNA fragment to the plasmid vector. To the resultant recombinant DNA was added 30 µl of "Epicurian Coli® XLI-Blue", a competent cell commercialized by Toyobo Co., Ltd., Tokyo, Japan, allowed to stand under ice-chilling conditions for 30 min, heated to 42° C., admixed with SOC broth, and incubated at 37° C. for one hour to introduce the recombinant DNA into *Escherichia coil*.

The transformant thus obtained was inoculated into agar plate (pH 7.0) containing 50 µg/ml of 5-bromo-4-chloro-3-indolyl-β-galactoside, and cultured at 37° C. for 18 hours, followed by placing a nylon film on the agar plate to fix thereon about 7,000 colonies formed on the agar plate. Based on the amino acid sequence Phe-Lys-Leu-Trp-Ala-Pro (amino acid 15–21 if SEQ ID NO:9), probe 1 represented by the base sequence of 5'-TTYAARYTNTGGGCNCC-3' (SEQ ID NO: 8) was chemically synthesized, labelled with $^{32}$P, and hybridized with the colonies of transformants fixed on the nylon film, followed by selecting 12 transformants which exhibited a strong hybridization.

The objective recombinant DNA was selected in usual manner from the 12 transformants, and, in accordance with the method described by E. M. *Southern in Journal of Molecular Biology*, Vol.98, pp.503–517 (1975), hybridized with prove 2 having the base sequence of 5'-CARTGGGTNGAYGAYTTYCA-3' (SEQ ID NO:9) which had been chemically synthesized based on the amino acid sequence of Gln-Trp-Val-Asp-Asp-Phe-His (amino acid 4–10 of) SEQ ID NO:4 and labelled with $^{32}$P, followed by selecting a recombinant DNA which exhibited a strong hybridization. The recombinant DNA and transformant were respectively named "pSU18" and "SU18".

The transformant SU18 was inoculated into L-broth (pH 7.0) containing 100 µg/ml ampicillin, and cultured at 37° C. for 24 hours with a rotary shaker. After completion of the culture, the cells were collected from the culture by centrifugation, and treated with the alkaline method in general to extracellularly extract the recombinant DNA. The resultant extract was in usual manner purified and analyzed to find that the recombinant DNA pSU18 consists of about 6,000 base pairs and has a DNA, which encodes the enzyme and consists of about 1,700 base pairs, in the downstream of the cleavage site of Ssp I, a restriction enzyme.

Experiment 3-3
Production of Recombinant Thermostable Enzyme by Transformant SU18

To 500-ml flasks were added about 100 ml aliquots of a liquid culture medium (pH 7.0) consisting of 0.1 w/v % polypeptone, 0.1 w/v % yeast extract, 0.2 w/v % ammonium sulfate, 0.05 w/v % potassium dihydrogen phosphate, 0.02 w/v % magnesium sulfate heptahydrate, 0.02 w/v % potassium chloride, and water. The flasks were sterilized by autoclaving at 120° C. for 20 min, cooled, admixed with 50 µg/ml ampicillin, and inoculated with a seed culture of transformant SU18 in Experiment 3-2, followed by culturing the transformant at 37° C. for 24 hours under a rotary shaking condition of 130 rpm to obtain a seed culture. About 5 L of a fresh preparation of the same liquid culture medium was placed in a 10-L fermenter, sterilized similarly as above, cooled to 37° C., admixed with 50 µg/ml ampicillin, inoculated with one v/v % of the seed culture, followed by the incubation at 37° C. for 24 hours under an aeration condition of 500 ml/min. The resultant culture was in usual manner treated with ultrasonic to disrupt cells, and the resultant suspension was centrifuged to remove insoluble substances, followed by assaying for enzymatic activity to reveal that one L of the culture contained about 30 units of the recombinant thermostable enzyme.

As a control, a seed culture of *Escherichia coli* XLI-Blue strain or *Sulfolobus acidocaldarius* (ATCC 33909) was inoculated into a fresh preparation of the same liquid culture medium but free of ampicillin. In the case of culturing *Sulfolobus acidocaldarius* (ATCC 33909), it was cultured and treated similarly as above except that the initial pH of the nutrient culture medium and the culturing temperature were respectively set to 3.0 and 75° C. Assaying the resultant enzymatic activity, one L culture of *Sulfolobus acidocaldarius* (ATCC 33909) yielded about 2 units of the thermostable enzyme, and the yield was significantly lower than that of transformant SU18. *Escherichia coli* XLI-Blue strain used as a host did not form the thermostable enzyme.

Thereafter, the recombinant thermostable enzyme produced by the transformant SU18 was purified similarly as in Experiments 1 and 2 and examined for properties and features and revealing that it has substantially the same physicochemical properties of the thermostable enzyme from *Sulfolobus acidocaldarius* (ATCC 33909) because (i) the recombinant thermostable enzyme has a molecular weight of about 54,000–64,000 daltons on SDS-PAGE and an isoelectric point of about 5.6–6.6 on isoelectrophoresis, and (ii) it is not substantially inactivated even when incubated in an aqueous solution (pH 7.0) at 85° C. for 60 min. These results indicate that the present thermostable enzyme can be prepared by the recombinant DNA technology with a significantly improved yield.

Experiment 4
Preparation of Complementary DNA, and Determination of Base Sequence and Amino Acid Sequence Two µg of the recombinant DNA pSU18 in Experiment 3-2 was weighed, degenerated by the addition of 2 M aqueous sodium hydroxide solution, and admixed with an adequate amount of cold ethanol, followed by collecting the resultant sediment containing a template DNA and drying the sediment in vacuo. To the template DNA were added 50 pmole/ml of a chemically synthesized primer having the base sequence of 5'-GTAAAACGACGGCCAGT-3' (SEQ ID NO:16) and 10 µl of 40 mM Tris-HCl buffer (pH 7.5) containing 20 mM magnesium chloride and sodium chloride, and the mixture was incubated at 65° C. for 2 min to effect annealing. The resultant mixture was admixed with 2 µl of an aqueous solution containing 7.5 µM dATP, dGTP and dTTP respectively, 0.5 µl of [α-$^{32}$P]dCTP (2 mCi/ml), one µl of 0.1 M dithiothreitol, and 2 µl of 1.5 units/ml T7 DNA polymerase, followed by the incubation at 25° C. for 5 min to extend the primer from the 5'-terminus to the 3'-terminus. Thus, a complementary chain DNA was obtained.

The reaction product containing the complementary chain DNA was divided into quarters, to each of which 2.5 µl of 50 mM aqueous sodium chloride solution containing 80 µM dNTP and 8 µM ddATP, ddCTP, ddGTP or ddTTP was added, and the resultant mixture was incubated at 37° C. for 5 min, followed by suspending the reaction by the addition of 4 µl of 98 v/v % aqueous formamide solution containing 20 mM EDTA, 0.05 w/v % bromophenol blue and 0.05 w/v % xylene cyanol. The reaction mixture was placed in a container, heated in a boiling-water bath for 3 min, placed on a gel containing 6 w/v % polyacrylamide, and electrophoresed by energizing the gel with a constant voltage of about 2,000 volts to separate DNA fragments, followed by fixing the gel in usual manner, drying it and subjecting the resultant to autoradiography.

Analyses of the DNA fragments separated on the radiogram revealed that the complementary chain DNA contains the base sequence consisting of about 1,700 base pairs in SEQ ID NO:5. An amino acid sequence that could be estimated from the base sequence was in SEQ ID NO:5, and it was compared with the partial amino acid sequences in SEQ ID NOs:3 and 4, and revealing that the partial amino acid sequence in SEQ ID NO:3 corresponded to that positioning from 1 to 30 in SEQ ID NO:5, and that in SEQ ID NO:4 corresponded to that positioning from 301 to 319 in SEQ ID NO:5. These results indicate that the present recombinant thermostable enzyme has the amino acid sequence from the N-terminal in SEQ ID NO:1, and, in the case of the DNA derived from *Sulfolobus acidocaldarius* (ATCC 33909), the amino acid sequence is encoded by the base sequence from the 5'-terminus in SEQ ID NO:2.

As is explained in the above, the thermostable enzyme, which releases trehalose from non-reducing saccharides having a trehalose structure as an end unit and a degree of glucose polymerization of at least 3, was found as a result of the present inventors' long-term research. The thermostable enzyme has distinct physicochemical properties from those of other conventional enzymes. The present invention is to produce the thermostable enzyme by using the recombinant DNA technology. The present recombinant thermostable enzyme, its preparation and uses will be explained in detail with reference to the later described Examples.

The recombinant thermostable enzyme as referred to in the present invention means thermostable enzymes in general which are preparable by the recombinant DNA technology and capable of releasing trehalose from non-reducing saccharides having a trehalose structure as an end unit and a degree of glucose polymerization of at least 3. Generally, the recombinant thermostable enzyme according to the present invention has a revealed amino acid sequence, and, as an example, the amino acid sequence from the N-terminal as shown in SEQ ID NO:1, and homologous ones to it can be mentioned. Variants having amino acid sequences homologous to the one in SEQ ID NO:1 can be obtained by replacing one or more bases in SEQ ID NO:1 with other bases without substantially alternating the inherent physicochemical properties. Although even when used the same DNA and it also depends on hosts into which the DNA is introduced, the ingredients and components of nutrient culture media for culturing transformants, and their cultivation temperature and pH, there may be produced modified enzymes which have the inherent physicochemical properties but defect one or more amino acids in SEQ ID NO:1, or those which have one or more amino acids added newly to the N-terminal after the DNA expression as the result of the modification of intracellular enzymes of the hosts. Such variants can be used in the present invention as long as they have the desired physicochemical properties.

The recombinant thermostable enzyme can be obtained from cultures of transformants containing a specific DNA. Examples of such transformants usable in the present invention can be prepared by introducing into hosts a DNA which has either the base sequence from the 5'-terminus in SEQ ID NO:2 or a homologous base sequence to it or a complementary base sequence to them. These base sequences may be modified by replacing one or more bases of them without alternating the amino acid sequences encoded by them by means of the degeneracy of genetic code. Needless to say, one or more bases in such base sequences which encode the recombinant thermostable enzyme or their variants can be readily replaced with other bases to allow the DNA to express the objective thermostable enzyme production in hosts.

The DNA usable in the present invention includes those are derived from natural resources and those which are artificially synthesized as long as they have the aforesaid base sequences. The natural resources for the DNA according to the present invention are, for example, microorganisms of the genus Sulfolobus such as *Sulfolobus acidocaldarius* (ATCC 33909), and from which genes containing the present DNA can be obtained. The aforementioned microorganisms can be inoculated in nutrient culture media and cultured for about 1–3 days under aerobic conditions, and the resultant cells were collected from the cultures and subjected to ultrasonication or treated with a cell-wall lysis enzyme such as lysozyme or β-glucanase to extract genes containing the present DNA. In this case, a proteolytic enzyme such as protease can be used along with the cell-wall lysis enzyme, and, when treated the cells with an ultrasonic disintegrator, they may be treated in the presence of a surfactant such as sodium dodecyl sulfate (SDS) or with freezing and thawing method. The objective DNA is obtainable by treating the resultant with phenol extraction, alcohol sedimentation, centrifugation, protease treatment and/or ribonuclease treatment generally used in this field. To artificially synthesize the present DNA, it can be chemically synthesized by using the base sequence in SEQ ID NO:2, or can be obtained in a plasmid form by inserting a DNA, which encodes the amino acid sequence in SEQ ID NO:1, into an appropriate self-replicable vector to obtain a recombinant DNA, introducing the recombinant DNA into an appropriate host to obtain a transformant, culturing the transformant, separating the proliferated cells from the resultant culture, and collecting plasmids containing the objective DNA from the cells.

Such a DNA is generally introduced into hosts in a recombinant DNA form. Generally, the recombinant DNA contains the aforesaid DNA and a self-replicable vector, and it can be prepared with a relative easiness by the recombinant DNA technology in general when the material DNA is in hand. Examples of such a vector are plasmid vectors such as pBR322, pUC18, Bluescript II SK(+), pUB110, pTZ4, pC194, pHV14, TRp7, TEp7, pBS7, etc.; and phage vectors such as λgt·λC, λgt·λB, ρ11, φ1, φ105, etc. Among these plasmid- and phage-vectors, pBR322, pUC18, Bluescript II SK(+), λgt·λC and λgt·λB are satisfactorily used when the present DNA should be expressed in *Escherichia coli*, while pUB110, pTZ4, pC194, ρ11, φ1 and φ105 are satisfactorily used to express the DNA in microorganisms of the genus Bacillus. The plasmid vectors pHV14, TRp7, TEp7 and pBS7 are advantageously used when the recombinant DNA is allowed to grow in 2 or more hosts.

The methods used to insert the present DNA into such vectors in the present invention may be conventional ones in generally used in this field. A gene containing the present DNA and a self-replicable vector are first digested with a restriction enzyme and/or ultrasonic, then the resultant DNA fragments and vector fragments are ligated. To digest DNAs and vectors, restriction enzymes which specifically act on nucleotides, particularly, type II restriction enzymes, more particularly Sau 3AI, Eco RI, Hind III, Bam HI, Sal I, Xba I, Sac I, Pst I, etc., facilitate the ligation of the DNA fragments and vector fragments. To ligate the DNA fragments with the vector fragments, they are, if necessary, annealed and subjected to the action of a DNA ligase in vivo or in vitro. The recombinant DNA thus obtained is replicable without substantial limitation by introducing it into appropriate hosts to form transformants and culturing the transformants.

The recombinant DNA thus obtained can be introduced into appropriate host microorganisms including *Escherichia coli* and those of the genus Bacillus as well as actinomyces and yeasts. In the case of using *Escherichia coli* as a host, the DNA can be introduced thereinto by culturing the host in the presence of the recombinant DNA and calcium ion, while in the case of using a microorganism of the genus Bacillus as a host the competent cell method and the colony hybridization method can be used. Desired transformants can be cloned by the colony hybridization method or by culturing a variety of transformants in nutrient culture media containing reducing amylaceous saccharides having a degree of glucose polymerization of at least 3, and selecting the objective transformants which release trehalose from non-reducing saccharides having a trehalose structure as an end unit and a degree of glucose polymerization of at least 3.

The transformants thus obtained intra- and extracellularly produce the objective enzyme when cultured in nutrient culture media. Generally, liquid culture media in general supplemented with carbon sources, nitrogen sources and minerals, and, if necessary, further supplemented with small amounts of amino acids and vitamins can be used in the invention. Examples of the carbon sources are saccharides such as unprocessed starch, starch hydrolysate, glucose, fructose, sucrose and trehalose. Examples of the nitrogen sources are organic- and inorganic-substances containing nitrogen such as ammonia and salts thereof, urea, nitrate, peptone, yeast extract, defatted soy been, corn steep liquor, and beef extract. Cultures containing the objective enzyme can be prepared by inoculating the transformants into nutrient culture media, and incubating them at a temperature of 20–65° C. and a pH of 2–9 for about 1–6 days under aerobic conditions by the aeration-agitation method. Such cultures can be used intact as a crude enzyme, and, usually, cells in the cultures may be disrupted prior to use with ultrasonic and/or cell-wall lysis enzymes, followed by separating the thermostable enzyme from intact cells and cell debris by filtration and/or centrifugation and purifying the enzyme. The methods to purify the enzyme include conventional ones in general. From cultures intact cells and cell debris are eliminated and subjected to one or more methods such as concentration, salting out, dialysis, separatory sedimentation, gel filtration chromatography, ion-exchange chromatography, hydrophobic chromatography, affinity chromatography, gel electrophoresis and isoelectric point electrophoresis.

As is described above, the recombinant thermostable enzyme according to the present invention has a specific feature of releasing trehalose from non-reducing saccharides having a trehalose structure as an end unit and a degree of glucose polymerization of at least 3 even when allowed to act on them at a temperature exceeding 55° C. The trehalose thus obtained has a satisfactorily-mild and high-quality sweetness as well as an adequate viscosity and moisture-retaining ability, and, as a great advantageous feature, they can sweeten food products without fear of causing unsatisfactory coloration and deterioration because they have no reducing residue within their molecules. With these features a variety of amylaceous saccharides, which have been put aside because of their reducibilities, can be converted into saccharides which have a satisfactory handleability, usefulness, and no substantial reducibility or extremely-reduced reducibility.

Explaining now the conversion method in more detail, non-reducing saccharides having a trehalose structure and a degree of glucose polymerization of at least 3 such as α-glucosyltrehalose, α-maltosyltrehalose, α-maltotriosyltrehalose, α-maltotetraosyltrehalose and α-maltopentaosyltrehalose. These non-reducing saccharides can be obtained by allowing a non-reducing saccharide-forming enzyme as disclosed in Japanese Patent Application No.349,216/93, applied by the present applicant and Japanese Patent Application Serial No.10046601, titled "Thermostable non-reducing saccharide-forming enzyme, its preparation and uses", applied by the same applicant on Jun. 24, 1994, to act on reducing amylaceous saccharides having a degree of glucose polymerization of at least 3 which are prepared by treating starch or amylaceous saccharides such as amylopectin and amylose with acids and/or amylases. These reducing saccharides usable as a substrate for the non-reducing saccharide-forming enzyme usually contain one or more maltooligosaccharides having a degree of glucose polymerization of at least 3, for example, maltotriose, maltotetraose, maltopentaose, maltohexaose and maltoheptaose. As is described in "Handbook of Amylases and Related Enzymes", 1st edition (1988), edited by The Amylase Research Society of Japan, published by Pergamon Press plc, Oxford, England, α-amylase, maltotetraose-forming amylase, maltopentaose-forming amylase and maltohexaose-forming amylase are especially useful to prepare the reducing amylaceous saccharides used in the present invention, and, the use of any one of these amylases facilitates the production of mixtures of amylaceous saccharides rich in reducing amylaceous saccharides having a degree of glucose polymerization of at least 3 in a considerably-high yield. If necessary, the combination use of the amylases and starch debranching enzymes such as pullulanase and isoamylase can increase the yield of the reducing amylaceous saccharides used as the substrate for the present recombinant thermostable enzyme. Non-reducing saccharides can be obtained in a desired amount by coexisting such a non-reducing saccharide-forming enzyme in aqueous solutions containing one or more reducing amylaceous saccharides up to 50 w/w %, and, usually, incubating the mixture solution at a temperature of 40–85° C. and a pH of about 4–8 until the non-reducing saccharides are produced.

In the enzymatic conversion method according to the present invention, the present recombinant thermostable enzyme is generally allowed to coexist in an aqueous solution containing one or more of the above non-reducing saccharides as a substrate, followed by the enzymatic reaction at a prescribed temperature and pH until a desired amount of trehalose is formed. Although the enzymatic reaction proceeds even at a concentration of about 0.1 w/w %, d.s.b., of a substrate, a concentration of 2 w/w % or higher, d.s.b., preferably, in the range of 5–50 w/w %, d.s.b., of a substrate can be satisfactorily used when used the present conversion method in an industrial-scale production. The temperature and pH used in the enzymatic reaction are set to within the range of which does not inactivate the recombinant thermostable enzyme and allows the enzyme to effectively act on substrates, i.e. a temperature of higher than 55° C. but not higher than 85° C., preferably, a temperature in the range of about 56–70° C., and a pH of 4–7, preferably, a pH in the range of about 5–6. The amount and reaction time suitable for the present recombinant thermostable enzyme are chosen depending on the enzymatic reaction condition. Thus, the present recombinant thermostable enzyme effectively converts non-reducing saccharides having a trehalose structure as an end unit and a degree of glucose polymerization of at least 3 into trehalose and glucose and/or maltooligosaccharides, e.g. the conversion rate increases up to about 99% when the enzyme acts on α-maltotriosyltrehalose. When either of amylases is allowed to act on starch hydrolysates in combination with the non-reducing saccharide-forming enzyme and the present thermostable enzyme, non-reducing saccharides are formed along with trehalose and glucose and/or maltooligosaccharides. Thus, saccharide compositions rich in trehalose are efficiently formed in a relatively-high yield.

The reaction mixtures obtained by the present conversion reaction can be used intact, and, usually, they are purified prior to use: Insoluble substances are eliminated from the reaction mixtures by filtration and centrifugation, and the resultant solutions are decolored with activated charcoals, desalted and purified on ion exchangers, and concentrated into syrupy products. Depending on their use, the syrupy products are dried in vacuo and spray-dried into solid products. In order to obtain products which substantially consist of non-reducing saccharides, the aforesaid syrupy products are subjected to one or more methods such as chromatography using an ion exchanger, activated charcoal and silica gel for saccharide separation, separatory sedimentation using alcohol and/or acetone, membrane filtration, fermentation by yeasts, and removal and decomposition of reducing saccharides by alkalis. The methods to treat a relatively-large amount of a reaction mixture are, for example, fixed bed- or pseudomoving bed-ion exchange chromatography as disclosed in Japanese Patent Laid-Open Nos.23,799/83 and 72,598/83, and such a method produces non-reducing saccharide-rich products on an industrial scale and in a considerably-high yield.

The trehalose and compositions containing it have a wide applicability to a variety of products which are apt to be readily damaged by the reducibility of saccharide sweeteners: For example, they can be satisfactorily used in food products, cosmetics and pharmaceuticals as a sweetener, taste-improving agent, quality-improving agent, stabilizer, filler, excipient and adjuvant.

The following Examples explain in detail the preparation of the present recombinant thermostable enzyme, and the enzymatic conversion method of non-reducing saccharides:

Example A-1
Preparation of Recombinant Thermostable Enzyme

In 500-ml flasks were placed about 100 ml aliquots of a liquid culture medium (pH 7.0) consisting of one w/v % polypeptone, 0.5 w/v % yeast extract, 0.5 w/v % sodium chloride, and water, and to each flask was sterilized by autoclaving at 120° C. for 20 min, and admixed with 50 μg/ml ampicillin. Thereafter, the flasks were cooled and inoculated with the transformant SU18 obtained by the method in Experiment 3-2, followed by the culture of the transformant at 37° C. for 24 hours under a rotary shaking condition of 130 rpm to obtain a seed culture. To 30-L fermenter was placed about 18 L of a fresh preparation of the same liquid culture medium, sterilized similarly as above, cooled to 37° C., admixed with 50 μg/ml ampicillin, and inoculated with one v/v % of the seed culture, followed by the culture at 37° C. for 24 hours under aeration and agitation conditions.

The resultant culture was treated with ultrasonic to disrupt cells, and the resultant suspension was centrifuged to remove insoluble substances, followed by assaying the enzymatic activity in the supernatant to find that one L of the culture contained about 350 units of the present recombinant thermostable enzyme. The culture supernatant was purified by the method in Experiment 1 to obtain an about 12 ml aqueous solution containing about 230 units/ml of the present recombinant thermostable enzyme having a specific activity of about 720 units/mg protein.

Example A-2 (a)
Preparation of Transformant

Recombinant DNA pSU18 obtained by the method in Experiment 3-2 was cleaved with restriction enzymes Ssp I and Ban III to obtain a DNA fragment consisting of about 720 base pairs of a base sequence of bases 22 through 740 of SEQ ID NO:2. The DNA fragment was admixed with and ligated to "Bluescript II SK(+)", a plasmid vector commercialized by Pharmacia LKB Biotechnology AB, Uppsala, Sweden, which had been cleaved with restriction enzymes Ssp I and Ban III, at 4° C. overnight in the presence of T4 DNA ligase to obtain a first recombinant DNA.

Five oligonucleotides, which were chemically synthesized in usual manner and had the following base sequences represented by 5'-CTGCAGTTTTTTAATAAAATCAGG-AGGA-3" (SEQ ID NO:11), 5'-AAAAATATGTTTTCG-TTCGGTGGAAAT-3' (SEQ ID NO:12), 5'-ATTTCCAC-CGAACGAAAA-3' (SEQ ID NO:13), CATATTTTTTC-CTCCTGA-3' (SEQ ID NO:14), and 5'-TTTTATTAAAA-AACTGCAG-3' (SEQ ID NO:15), were mixed in an appropriate ratio, and the mixture was successively incubated at 100° C., 65° C., 37° C. and 20° C. for each 20 min to anneal them. The resultant base sequence in SEQ ID NO:6 and a double strand DNA consisting of 55 base pairs of bases 1 through 21 of SEQ ID NO:6 were ligated similarly as above with the first recombinant DNA which had been cleaved with Ssp I as a restriction enzyme to obtain a second recombinant DNA having the base sequence in SEQ ID NO:6 and a base sequence of bases 1 through 740 of SEQ ID NO:2.

Recombinant DNA pSU18 obtained by the method in Experiment 3-2 was cleaved with restriction enzymes Ban III and Bst XI, and the resultant DNA fragment consisting of about 1,600 base pairs of a base sequence of bases 741 through 1,668 of SEQ ID NO: 2 was ligated with "Bluescript II SK(+)", a plasmid vector which had been cleaved with restriction enzymes Ban III and Bst XI to obtain a third recombinant DNA.

Five oligonucleotides, which were chemically synthesized in usual manner, having the following base sequences represented by 5'-AACAGAGGTGTTGGG-3' (SEQ ID NO:16), 5'-GTATATCAATTAGAATGAAGCTTGAGCT-3' (SEQ ID NO:17), 5'-CAAGCTTCATTCTA-3 (SEQ ID NO:18), and 5'-ATTGATATACCCCAACACCTCTGTT-3' (SEQ ID NO:19) were mixed in an appropriate ratio, and the mixture was annealed similarly as above. The resultant double strand DNA having the base sequence in SEQ ID NO:7 consisting of 40 base pairs of bases 1,639 through 1,668 of SEQ ID NO:2 was ligated to the third recombinant DNA which had been cleaved with restriction enzymes Hpa I and Sac I to obtain a fourth recombinant DNA having the base sequence in SEQ ID NO:7 and a base sequence of bases 741 through 1,668 of SEQ ID NO:2.

A DNA fragment which consists of about 770 base pairs, having a base sequence of bases 1 through 740 of SEQ ID NO:2, that had been obtained by cleaving the second recombinant DNA with restriction enzymes Pst I and Ban III, and a DNA fragment which consists of about 930 base pairs having a base sequence of bases 741 through 1,668 of SEQ ID NO:2, that had been obtained by cleaving the fourth recombinant DNA with restriction enzymes Ban III and Hind III, were ligated to "pKK223-3", which had been cleaved with restriction enzymes Pst I and Hind III, with T4 DNA ligase to obtain the present recombinant DNA pSU19 having the base sequence in SEQ ID NO:2.

Figure 6:
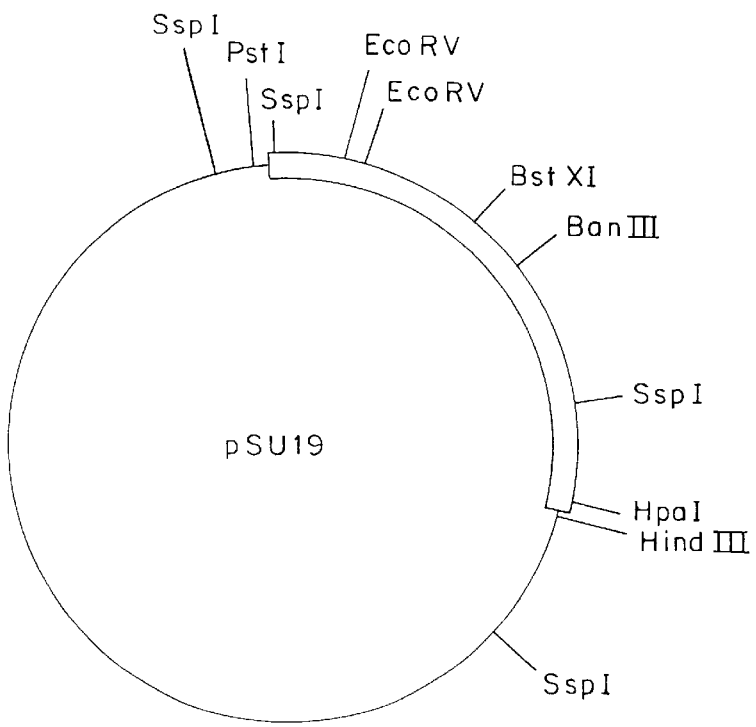
FIG. 6 is a restriction map of the recombinant DNA pSU19 according to the present invention.

In accordance with the method in Experiment 3-2, the recombinant DNA pSU19 was introduced into "BMH71-18", a competent cell commercialized by Takara Shuzo Co., Ltd., Tokyo, Japan, to obtain transformant SU19 having a DNA encoding the present recombinant thermostable enzyme. The transformant SU19 was cultured by the method in Experiment 3-2, and the proliferated cells were collected from the resultant culture. A recombinant DNA was extracted from the cells and analyzed and revealing that it consists of about 6,300 base pairs, and, as shown in FIG. 6, it has a DNA consisting of 1,668 base pairs located in the downstream of the cleavage site of Ssp I, a restriction enzyme.

Example A-2 (b)
Preparation of Recombinant Thermostable Enzyme from Transformant The transformant SU19 in Example A-2 (a) was cultured similarly as in Example A-1 except that a liquid nutrient culture medium (pH 7.0) consisting of 2 w/v % maltose, 4 w/v % "N-Z-SOY PEPTONE commercialized by Sigma Chemicals Co., St. Louis, Mo., USA, 2 w/v % yeast extract, 0.5 w/v % sodium dihydrogen phosphate, 50 μg/ml ampicillin, and water was used. The resultant culture was treated with ultrasonic to disrupt cells, and the cell suspension was centrifuged to remove insoluble substances, followed by assaying the recombinant thermostable enzyme activity in the resultant supernatant and revealing that one L culture yielded about 800,000 units of the objective recombinant thermostable enzyme. The supernatant was purified by the method in Experiment 1 to obtain an about 1,850 ml aqueous solution containing about 3,200 units/ml of the recombinant thermostable enzyme with a specific activity of about 720 units/mg protein.

The purified enzyme was assayed for properties and features by the method in Experiment 2 and revealing that it had a molecular weight of about 54,000–64,000 daltons on SDS-PAGE and a pI of about 5.6–6.6 on isoelectrophoresis, and was not substantially inactivated even when incubated in an aqueous solution (pH 7.0) at 85° C. for 60 min. These physicochemical properties were substantially the same as those of the thermostable enzyme from a donor microorganism of *Sulfolobus acidocaldarius* (ATCC 33909).

Example B-1 (a)
Conversion into Syrupy Product Containing Trehalose

To 500-ml flasks were added about 100 ml aliquots of a liquid culture medium consisting of 0.1 w/v % polypeptone, 0.1 w/v % yeast extract, 0.2 w/v % ammonium sulfate, 0.05 w/v % potassium dihydrogen phosphate, 0.02 w/v % magnesium sulfate heptahydrate, 0.02 w/v % potassium chloride, and water. The flasks were sterilized by autoclaving at 120° C. for 20 min, cooled and adjusted its pH to 3.0 by the addition of sulfuric acid. A seed culture of *Sulfolobus acidocaldarius* (ATCC 33909) was inoculated to the flasks, and cultured at 75° C. for 24 hours under a rotatory shaking condition of 130 rpm to obtain a first seed culture. About 5 L of a fresh preparation of the same liquid culture medium was placed in a 10-L fermenter, sterilized similarly as above, cooled to 75° C., adjusted to pH 3.0, inoculated with one v/v % of the seed culture, followed by the incubation at 75° C. for 24 hours under an aeration condition of 500 ml/min to obtain a second seed culture. Thereafter, about 250 L of a fresh preparation of the same liquid culture medium in a 300-L fermenter, sterilized similarly as above, cooled to 75° C., and cultured under aeration and agitation conditions of 100 L/min for 42 hours.

About 170 L of the resultant culture was filtered with an SF membrane, and the filtrate was centrifuged to obtain wet cells, and about 258 g of which was suspended in 300 ml of 10 mM phosphate buffer (pH 7.0) and ultrasonicated to disrupt the cells. The cell debris thus obtained was centrifuged at 10,000 rpm for 30 min, and about 300 ml of the resultant supernatant was mixed with ammonium sulfate to give a saturation degree of 70 w/v %, allowed to stand at 4° C. for 24 hours, and centrifuged at 10,000 rpm for 30 min. The precipitate was collected, dissolved in an adequate amount of 10 mM Tris-HCl buffer (pH 8.5), and dialyzed against a fresh preparation of the same buffer for 24 hours. Thereafter, the dialyzed solution was centrifuged at 10,000 rpm for 30 min to obtain an about 300 ml of a supernatant with an enzymatic activity.

The supernatant was fed to a column packed with about 360 ml of "DEAE-TOYOPEARL®", a gel for ion-exchange column chromatography commercialized by Tosoh Corporation, Tokyo, Japan, which had been previously equilibrated with 10 mM Tris-HCl buffer (pH 8.5), and fed with a linear gradient buffer raging from 0 M to 0.3 M in 10 mM Tris-HCl buffer (pH 8.5). Fractions with an enzymatic activity, eluted at a concentration of about 0.1 M sodium chloride, were collected, pooled, and dialyzed for 10 hours against 10 mM Tris-HCl buffer (pH 8.5) containing one M ammonium sulfate. The dialyzed solution was centrifuged at 10,000 rpm for 30 min to remove insoluble substances, fed to a column packed with about 350 ml of "BUTYL-TOYOPEARL® 650", a gel for hydrophobic chromatography commercialized by Tosoh Corporation, Tokyo, Japan, which had been previously equilibrated with 10 mM Tris-HCl buffer (pH 8.5) containing one M ammonium sulfate, and fed with a linear gradient buffer ranging from 1 M to 0 M ammonium sulfate in 10 MM Tris-HCl buffer (pH 8.5). Fractions with an enzymatic activity eluted at about 0.8 M ammonium sulfate were collected, pooled, dialyzed for 16 hours against 10 mM Tris-HCl buffer (pH 8.5) containing 0.2 M sodium chloride, and centrifuged at 10,000 rpm for 30 min to remove insoluble substances. The resultant supernatant was fed to a column packed with about 350 ml of "TOYOPEARL® HW-55", a gel for gel chromatography commercialized by Tosoh Corporation, Tokyo, Japan, which had been previously equilibrated with 10 mM Tris-HCl buffer (pH 8.5) containing 0.2 M sodium chloride. Fractions with an enzymatic activity were collected from the eluate, pooled, and dialyzed against 10 mM Tris-HCl buffer (pH 8.5) for 16 hours. The dialyzed solution was centrifuged to remove insoluble substances, and the supernatant was subjected to hydrophobic column chromatography using "MONO Q", a gel for ion-exchange chromatography commercialized by Pharmacia LKB Uppsala, Sweden, followed by feeding to the column with a linear gradient buffer ranging from 0 M to 0.2 M of sodium chloride in 10 mM Tris-HCl buffer (pH 8.5). The fractions eluted at about 0.1 M sodium chloride were collected and pooled for the production of trehalose. The purified non-reducing saccharide-forming enzyme thus obtained had a specific activity of about 81 units/mg protein, and the yield was about 0.24 units per one L of the culture.

Throughout the specification the activity of a non-reducing saccharide-forming enzyme is expressed by the value measured on the following assay: Place 4 ml of 50 mM acetate buffer (pH 5.5) containing as a substrate 1.25 w/v % maltopentaose in a test tube, add one ml of an adequately diluted enzyme solution to the test tube, and incubate the mixture solution at 60° C. for 60 min to effect enzymatic reaction and heated at 100° C. for 30 min to suspend the enzymatic reaction. Thereafter, one ml of the reaction mixture was diluted with deionized water by 10 times and assayed for reducing power on the Somogyi-Nelson's method. As a control, a system using an enzyme solution, which has been heated at 100° C. for 30 min to inactivate the enzyme, is provided and similarly treated as above. One unit activity of the non-reducing saccharide-forming enzyme is defined as the amount of enzyme which diminishes the reducing power of one $\mu$mol maltopentaose per min under the same conditions as mentioned above.

Example B-1 (b)
Conversion into Syrupy Product Containing Trehalose

Corn starch was suspended in water into a 15 w/w % suspension which was then admixed with 0.1 w/w % calcium carbonate. The mixture was adjusted to pH 6.0, admixed with 0.2 w/w % of "TERMAMYL 60L", an α-amylase specimen commercialized by Novo Nordisk Bioindustri A/S, Copenhagen, Denmark, to starch, d.s.b., and enzymatically reacted at 95° C. for 15 hours to gelatinize and liquefy the starch. The reaction mixture was autoclaved at 120° C. for 30 min to inactivate the remaining enzyme, cooled to 58° C., adjusted to pH 5.5, admixed with 3,000 units/g starch, d.s.b., of an isoamylase specimen, 3.0 units/g starch, d.s.b., of a recombinant thermostable enzyme obtained by the method in Example B-1 (a), and 5.0 units/starch, d.s.b., of a recombinant thermostable enzyme obtained by the method in Example A-1, and enzymatically reacted for 64 hours. The resultant reaction mixture was heated at 97° C. for 30 min to inactivate the remaining enzyme, cooled and filtered, and the resultant filtrate was in usual manner decolored with an activated charcoal, desalted and purified with an ion exchanger and concentrated to obtain an about 60 w/w % syrup in a yield of about 90% to the material starch, d.s.b.

The syrup had a relatively-low DE (dextrose equivalent) and contained 71.0 w/w % trehalose, 2.9 w/w % glucosyltrehalose, 1.0 w/w % maltosyltrehalose, 4.9 w/w % glucose, 10.5 w/w % maltose, 8.2 w/w % maltotriose and 1.5 w/w % maltotetraose and higher maltooligosaccharides, d.s.b. The product, having a mild and moderate sweetness as well as an adequate viscosity and moisture-retaining ability, can be satisfactorily used in compositions in general such as food products, cosmetics and pharmaceuticals as a sweetener, taste-improving agent, quality-improving agent, stabilizer, filler, excipient and adjuvant.

Example B-2
Conversion into Powdery Product Containing Trehalose

A syrupy product in Example B-1 was column chromatographed using a strong-acid cation exchange resin to increase the trehalose content. The procedures were as follows: Four jacketed-stainless steel columns, 5.4 cm in diameter and 5 m in length each, were packed to homogeneity with "XT-1016 (Na$^+$-form)", a strong-acid cation exchange resin commercialized by Tokyo Organic Chemical Industries, Ltd., Tokyo, Japan, which had been previously suspended in water, and cascaded in series to give a total column length of 20 m. The columns were fed with the syrupy product, adequately diluted with water, in a volume of about 5 v/v % to the resin and at an inner column temperature of 55° C., and fed with 55° C. hot water at an SV (space velocity ) 0.13 to elute saccharide components. Fractions rich in trehalose were collected, pooled, concentrated, dried in vacuo and pulverized to obtain a powdery product containing about 97 w/w % trehalose in a yield of about 55 w/w % to the material, d.s.b.

The product has a mild and moderate sweetness as well as no substantial reducibility, and can be satisfactorily used in compositions in general such as food products, cosmetics and pharmaceuticals as a sweetener, taste-improving agent, quality-improving agent, stabilizer, filler, excipient and adjuvant.

Example B-3
Conversion into Syrupy Product Containing Non-reducing Saccharide A fraction rich in trehalose obtained by the method in Example B-2 was concentrated into an about 75 w/w % solution which was then transferred to a crystallizer, and crystallized under gently stirring conditions to obtain a massecuite with a crystallization percentage of about 45 w/w %, d.s.b. The massecuite was sprayed downward from a nozzle equipped on the upper part of a spraying tower at a pressure of about 150 kg/cm$^2$ while an about 85° C. hot air was blowing downward from the upper part of the spraying tower, and the formed crystalline powder was collected on a wire-netting conveyer provided on the basement of the drying tower and gradually conveyed out of the spraying tower while an about 45° C. hot air was blowing to the crystalline powder from under the conveyer. The crystalline powder thus obtained was transferred to an ageing tower and aged for 10 hours in a stream of about 40° C. hot air to complete the crystallization and drying. Thus, a powdery hydrous crystalline trehalose was obtained in a yield of about 90 w/w % to the material, d.s.b.

The product has a mild and high-quality sweetness as well as substantial no hygroscopicity, and can be suitably incorporated into compositions in general such as food products, cosmetics and pharmaceuticals as a sweetener, taste-improving agent, quality-improving agent, stabilizer, filler, excipient, and adjuvant.

Example B-4
Conversion into Powdery Product Containing Crystalline Trehalose Tapioca starch was dissolved in water into a 36 w/w % suspension which was then admixed with 0.1 w/w % calcium carbonate. The mixture was adjusted to pH 6.0, admixed with 0.2 w/w % of "TERMAMYL 60L", an α-amylase specimen commercialized by Novo Nordisk Bioindustri A/S, Copenhagen, Denmark, to starch, d.s.b., and enzymatically reacted at 95° C. for 15 min to gelatinize and liquefy the starch. The mixture was autoclaved at 120° C. for 30 min to inactivate the remaining enzyme, cooled to 58° C., adjusted to pH 5.2, admixed with 2,000 units/g starch, d.s.b., of an isoamylase specimen commercialized by Hayashibara Biochemical Laboratories, Inc., Okayama, Japan, 2.5 units/g starch, d.s.b., of a thermostable enzyme obtained by the method in Example B-1 (a), 5.0 units/g starch, d.s.s.b, of a recombinant thermostable enzyme obtained by the method in Example A-1, and subjected to an enzymatic reaction for 72 hours. The reaction mixture was heated at 97° C. for 30 min to inactivate the remaining enzyme, cooled to 50° C., admixed with 10 units/g starch, d.s.b., of "GLUCOZYME", Nagase Biochemicals, Ltd., Kyoto, Japan, and subjected to an enzymatic reaction for 40 hours. The reaction mixture thus obtained was heated at 95° C. for 10 min to inactivate the remaining enzyme, cooled, filtered, decolored in usual manner with an activated charcoal, desalted and purified with ion exchangers, and concentrated into an about 60 w/w % syrup to obtain a syrupy product containing about 75.5 w/w % trehalose, d.s.b.

The syrupy product was concentrated into an about 84 w/w % solution which was then transferred to a crystallizer, admixed with about 2 w/w %, d.s.b., of hydrous crystalline trehalose as a seed crystal, and crystallized under gentle stirring conditions to obtain a massecuite with a crystallization percentage of about 45 w/w %, d.s.b. The massecuite was distributed to plastic plane vessels, allowed to stand at ambient temperature for 3 days to solidify and age the contents. Thereafter, the formed blocks were removed from the vessels, powdered by a pulverizer to obtain a solid product containing hydrous crystalline trehalose in a yield of about 90 w/w % to the material starch, d.s.b.

The product has a mild and high-quality sweetness as well as substantial no hygroscopicity, and can be suitably incorporated into compositions in general such as food products, cosmetics and pharmaceuticals as a sweetener, taste-improving agent, quality-improving agent, stabilizer, filler, excipient, and adjuvant.

Example B-5
Conversion into Powder Product Containing Crystalline Trehalose

Potato starch was suspended in water into a 6 w/w % suspension which was then admixed with 0.01 w/w % "NEO-SPITASE", an α-amylase specimen commercialized by Nagase Biochemicals, Ltd., Kyoto, Japan, adjusted to pH 6.2, and subjected to an enzymatic reaction at a temperature of 85–90° C. for one hour to gelatinize and liquefy the starch. The mixture was heated at 120° C. for 10 min to inactivate the remaining enzyme, cooled to 60° C., adjusted to pH 5.5, admixed with 500 units/g starch, d.s.b., of "PROMOZYME 200L", a pullulanase specimen commercialized by Novo Nordisk Bioindustri A/S, Copenhagen, Denmark, 3.0 units/g starch, d.s.b., of a thermostable non-reducing saccharide-forming enzyme obtained by the method in Example B-1 (a), 5.0 units/g starch, d.s.b., of a recombinant thermostable enzyme obtained by the method in Example A-1, and subjected to an enzymatic reaction for 48 hours. The reaction mixture was heated at 97° C. for 30 min to inactivate the remaining enzyme, adjusted to 50° C. and to pH 5.0, admixed with 10 units/g starch, d.s.b., of "GLUCOZYME", Nagase Biochemicals, Ltd., Kyoto, Japan, and subjected to an enzymatic reaction for 40 hours. The reaction mixture thus obtained was heated at 95° C. for 10 min to inactivate the remaining enzyme, cooled, filtered, decolored in usual manner with an activated charcoal, desalted and purified with ion exchangers, and concentrated into an about 60 w/w % syrup to obtain a syrupy product containing about 79.3 w/w % trehalose, d.s.b.

The syrupy product was column chromatographed similarly as in Example B-2 except that "C6000", commercialized by Japan Organo Co., Ltd., Tokyo, Japan, was used a strong-acid cation exchange resin in Na$^+$-form, followed by collecting a fraction containing about 95 w/w % trehalose, d.s.b. The fraction was concentrated up to about 75 w/w % and crystallized similarly as in Example B-4 to obtain a massecuite in the from of block which was then pulverized to obtain a powdery product containing hydrous crystalline trehalose in a yield of about 70 w/w % to the material starch, d.s.b.

The product is substantially free of hygroscopicity and readily handleable, and can be suitably incorporated into compositions in general such as food products, cosmetics and pharmaceuticals as a sweetener, taste-improving agent, quality-improving agent, stabilizer, filler, excipient, and adjuvant.

Example B-6

Conversion into Powdery Product Containing Anhydrous Crystalline Trehalose

One part by weight of "EX-I", an amylose product commercialized by Hayashibara Biochemical Laboratories, Inc., Okayama, Japan, was dissolved by heating in 15 parts by weight of water, and the solution was adjusted to 65° C. and pH 5.5, admixed with 2.0 units/g amylose, d.s.b., of a thermostable non-reducing saccharide-forming enzyme obtained by the method in Example B-1 (a) and 6.0 units/g amylose, d.s.b., of a recombinant thermostable enzyme obtained by the method in Example A-2, and subjected to an enzymatic reaction for 48 hours. The reaction mixture was incubated at 97° C. for 30 min to inactivate the remaining enzyme, adjusted to 50° C. and pH 5.0, admixed with 10 units/g amylose, d.s.b., "GLUCOZYME", a glucoamylase specimen commercialized by Nagase Biochemicals, Ltd., Kyoto, Japan, and incubated for another 40 hours. The newly formed reaction mixture was heated at 95° C. for 10 min to inactivate the remaining enzyme, cooled, filtered in usual manner, decolored with an activated charcoal, deionized and purified with an ion exchanger, and concentrated up to give a concentration of about 60 w/w % to obtain a syrupy product containing 82.2 w/w % trehalose, d.s.b.

The syrupy product was similarly as in Example B-5 subjected to column fractionation to obtain a fraction containing 98 w/w % trehalose, d.s.b., which was then concentrated by heating under a reduced pressure up to give a concentration of about 85 w/w %. To the concentrate was added about 2 w/w % anhydrous crystalline trehalose as a seed, followed by mixing the resultant at 120° C. for 5 min under stirring conditions. The resultant mixture was distributed to plastic plain vessels, and crystallized by drying in vacuo at 100° C. Thereafter, products in the form of a block were removed from the vessels, pulverized with a cutter to obtain a solid product, which contained anhydrous crystalline trehalose and had a moisture content of about 0.3 w/w % and a crystallization percentage of about 70 w/w %, in a yield of about 70% to the material amylose, d.s.b.

Anhydrous crystalline trehalose absorbs moisture from anhydrous substances to convert into hydrous crystalline trehalose, and because of this the product rich in such anhydrous crystalline trehalose is useful as a desiccant to dehydrate compositions such as food products, cosmetics and pharmaceuticals, and their materials and intermediates. The product with a mild and high-quality sweetness can be arbitrarily incorporated into compositions in general such as food products, cosmetics and pharmaceuticals as a sweetener, taste-improving agent, quality-improving agent, stabilizer, filler, diluent and excipient.

As is described above, the present invention is based on the finding of a novel thermostable enzyme which releases trehalose from non-reducing saccharides having a trehalose structure as an end unit and a degree of glucose polymerization of at least 3. The present invention is to explore a way to produce such a thermostable enzyme in an industrial scale and in a relatively-high efficiency by the recombinant DNA technology. The present conversion method using the recombinant thermostable enzyme readily converts non-reducing amylaceous saccharides, which have a trehalose structure as an end unit and a degree of glucose polymerization of at least 3, into trehalose and glucose and/or maltooligosaccharides without fear of causing bacterial contamination. The trehalose has a mild and high-quality sweetness, and, because it has no reducing residue within the molecule, it can be advantageously incorporated into compositions in general such as food products, cosmetics and pharmaceuticals without fear of causing unsatisfactory coloration and deterioration. The present recombinant thermostable enzyme is one which has a revealed amino acid sequence, so that it can be used freely in the preparation of trehalose that is premised to be used in food products and pharmaceuticals.

Thus, the present invention is a significant invention which exerts the aforesaid satisfactory effects and greatly contributes to this field.

While there has been described what is at present considered to be the preferred embodiments of the invention, it will be understood that various modifications may be made therein, and it is intended to cover in the appended claims all such modifications as fall within the true spirit and scope of the invention.

We claim:

1. An isolated DNA molecule encoding a thermostable enzyme having the following physico-chemical properties:

(1) Action

Releasing trehalose from non-reducing saccharides having a trehalose structure as an end unit and a degree of glucose polymerization of at least 3, but not substantially acting on maltooligosaccharides having a degree of glucose polymerization of at least 3;

(2) Molecular weight

About 54,000–64,000 daltons on sodium dodecyl sulfate polyacrylamide gel electrophoresis (SDS-PAGE); and (3) Thermostability Substantially not inactivated even when incubated in an aqueous solution (pH 7.0) at 85° C. for 60 min, wherein said DNA molecule has a base sequence selected from the group consisting of SEQ ID NO:2 and a sequence similar to SEQ ID NO:2 where one or more bases in SEQ ID NO:2 is replaced with a different base without altering the corresponding amino acid sequence of SEQ ID NO:1.

2. The isolated DNA molecule according to claim 1, wherein said one or more bases in said base sequence is replaced with a different base on the basis of the degeneracy of the genetic code.

3. The isolated DNA molecule according to claim 1, which is derivable from a microorganism of the genus Sulfolobus.

4. A replicable recombinant DNA molecule comprising a self-replicable vector and an isolated DNA molecule according to claim 1.

5. A host cell transformed with a replicable recombinant DNA molecule according to claim 4.

6. The transformed host cell according to claim 5, which is *Escherichia coli*.

7. A process for preparing a recombinant thermostable enzyme, comprising the steps of:

culturing a host cell according to claim 5 to express and produce the recombinant thermostable enzyme; and collecting the expressed and produced recombinant thermostable enzyme to prepare the recombinant thermostable enzyme.

8. The replicable recombinant DNA as claimed in claim 4, wherein said self-replicable vector is a plasmid vector, which is a colony-producing phagemid having a f1 origin of replication from the f1 filamentous phase that allows for rescue of the sense (+) strand, a ColE1 origin of replication, an amplicillin resistance marker gene, and a T3 RNA polymerase promoter linked to lacZ gene by a polylinker with multiple cloning sites.

9. The isolated DNA molecule according to claim 1, wherein said encoded thermostable enzyme has the amino acid sequence of SEQ ID NO:1, where one amino acid residue in SEQ ID NO:1 is replaced with a different amino acid.

10. An isolated recombinant DNA molecule comprising a nucleotide sequence encoding a thermostable enzyme having the following physico-chemical properties:

(1) Action

Releasing trehalose from non-reducing saccharides having a trehalose structure as an end unit and a degree of glucose polymerization of at least 3, but not substantially acting on maltooligosaccharides having a degree of glucose polymerization of at least 3;

(2) Molecular weight

About 54,000–64,000 daltons on sodium dodecyl sulfate polyacrylamide gel electrophoresis (SDS-PAGE); and (3) Thermostability Substantially not inactivated even when incubated in an aqueous solution (pH 7.0) at 85° C. for 60 min, and wherein said encoded thermostable enzyme has the amino acid sequence of SEQ ID NO:1, or a variant thereof which has the same physico-chemical properties as the thermostable enzyme of SEQ ID NO:1.

11. The isolated DNA molecule according to claim 10, wherein said encoded thermostable enzyme has an amino acid sequence of SEQ ID NO:1, and sequence identity thereto, wherein said sequence identity encodes a thermostable enzyme having the same physico-chemical properties of the enzyme encoded by SEQ ID NO:2.

12. The isolated DNA molecule according to claim 10, wherein said nucleotide sequence is selected from the group consisting of SEQ ID NO:2 and a sequence having sequence similarity to SEQ ID NO:2 where one or more nucleotides in SEQ ID NO:2 are replaced with different nucleotides on the basis of the degeneracy of the genetic code without altering the corresponding amino acid sequence of SEQ ID NO:1.

13. The isolated DNA molecule according to claim 10, which is derivable from a microorganism of the genus Sulfolobus.

14. A replicable recombinant DNA molecule comprising a self-replicable vector and an isolated DNA molecule according to claim 10.

15. A host cell transformed with a replicable recombinant DNA molecule according to claim 14.

16. The transformed host cell according to claim 5, which is *Escherichia coli*.

17. A process for preparing a recombinant thermostable enzyme, comprising the steps of:
   culturing a host cell according to claim 15 to express and produce the recombinant thermostable enzyme; and
   collecting the expressed and produced recombinant thermostable enzyme to prepare the recombinant thermostable enzyme.

\* \* \* \* \*